United States Patent
Dow et al.

(10) Patent No.: US 6,939,867 B2
(45) Date of Patent: Sep. 6, 2005

(54) β³ AGONISTS AND USES THEREOF

(75) Inventors: Robert L. Dow, Waterford, CT (US); Ernest S. Paight, Pawcatuck, CT (US)

(73) Assignee: Pfizer Inc., New York, NY (US)

( * ) Notice: Subject to any disclaimer, the term of this patent is extended or adjusted under 35 U.S.C. 154(b) by 439 days.

(21) Appl. No.: 10/086,588

(22) Filed: Feb. 28, 2002

(65) Prior Publication Data

US 2002/0128247 A1 Sep. 12, 2002

Related U.S. Application Data

(60) Provisional application No. 60/272,681, filed on Mar. 1, 2001.

(51) Int. Cl.$^7$ ............................. A61P 1/00; A61P 25/00; A61K 31/55; A61K 31/535; A61K 31/44; A61K 31/42; C07D 401/00; C07D 413/00; C07D 221/22; C07D 263/00

(52) U.S. Cl. ................. 514/63; 514/217.04; 514/235.5; 514/253.01; 514/278; 514/295; 514/309; 514/318; 514/326; 514/331; 514/336; 514/339; 514/343; 514/357; 514/376; 514/600; 540/597; 544/131; 544/360; 546/14; 546/17; 546/97; 546/141; 546/194; 546/209; 546/232; 546/276.7; 546/279.1; 546/283.4; 546/334; 548/229; 564/79

(58) Field of Search ............................. 514/63, 217.04, 514/235.5, 253.01, 278, 295, 309, 318, 326, 331, 336, 339, 343, 357, 376, 600; 540/597; 544/131, 360; 546/14, 17, 97, 141, 194, 209, 232, 276.7, 279.1, 283.4, 334; 548/229; 564/79

(56) References Cited

U.S. PATENT DOCUMENTS

| | | | |
|---|---|---|---|
| 4,358,455 A | 11/1982 | Atkinson et al. | ............ 424/263 |
| 4,478,849 A | 10/1984 | Ainsworth et al. | ......... 424/285 |
| 5,019,578 A | 5/1991 | Fisher et al. | ................ 514/275 |
| 5,030,640 A | 7/1991 | Fisher et al. | ................ 514/339 |
| 5,153,210 A | 10/1992 | Ainsworth et al. | ......... 514/369 |
| 5,705,515 A | 1/1998 | Fisher et al. | ................ 514/365 |
| 5,776,983 A | 7/1998 | Washburn et al. | ........... 514/605 |
| 5,792,871 A | 8/1998 | Chartrain et al. | ........... 546/335 |
| 5,977,124 A | 11/1999 | Dow | .......................... 514/272 |

FOREIGN PATENT DOCUMENTS

| | | | |
|---|---|---|---|
| EP | 0516349 | 12/1992 | ......... C07C/217/18 |
| WO | WO9529159 | 2/1995 | ......... C07D/213/30 |
| WO | WO9804526 | 2/1998 | ......... C07D/209/04 |
| WO | WO9965877 | 12/1999 | ......... C07D/213/80 |
| WO | WO0206274 | 1/2002 | ......... C07D/401/12 |

OTHER PUBLICATIONS

Tesfamariam, B. et al., "β1—and β2–Adrenoceptor Antagonist Activities of ICI–215001, a Putative β3–Adrenoceptor Agonist", 1 55–58 (1994).

Martin, et al., "Effects of Two β3–Adrenoceptor Agonists, SR 58611A and BRL 37344, and of Salbutamol on Cholinergic and NAN Neural Contraction in Guinea–pig Main Bronchi in vitro", 110, 1311–1316 (1993).

Giudice, et al., "Inhibition of Rat Colonic Motility and Cardiovascular Effects of New Gut–Specific Beta–Adrenergic Phenylethanolaminotetralines", 44, 1411–1417(1989).

Simland, et al., "Antidepressant Profile in Rodents of SR 58611A, a New Selective Agonist for Atypical β–adrenoceptors", 219, 19 201(1992).

Taneja, et al., "Evidence for a Noradrenergic innervation to "Atypical" Beta Adrenoceptors (or Putative Beta–3 Adrenoceptors) the lieum of Guinea Pig", 260, 192–200 (1992).

Krief, et al., "Tissue Distribution of β3–adrenergic Receptor mRNA in Man", 91 344–349 (1993).

*Primary Examiner*—Brenda Coleman
(74) *Attorney, Agent, or Firm*—Peter C. Richardson; Gregg C. Benson; Arlene K. Musser

(57) ABSTRACT

Sulfamide compounds having formula (I) are described as well as their use in the treatment of diseases dependent on the signaling pathways associated with β-adrenergic receptors, such as obesity, diabetes, hypertension, gastrointestinal hypo- or hyper-motility and cardiovascular diseases

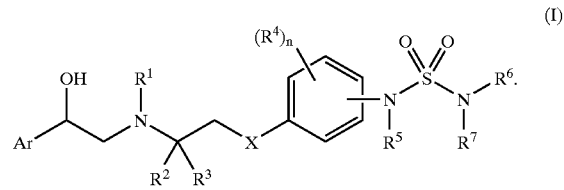

(I)

47 Claims, No Drawings

β³ AGONISTS AND USES THEREOF

This application claims the benefit of U.S. Provisional Patent Application No. 60/272,681, filed Mar. 1, 2001, incorporated herein by reference in its entirety.

FIELD OF THE INVENTION

The present invention relates to sulfamide compounds that act as selective $\beta_3$ agonists, pharmaceutical compositions comprising the sulfamide compounds, and their use in the treatment of diseases dependent on the signaling pathways associated with β-adrenergic receptors, such as obesity, diabetes, hypertension, gastrointestinal hypo- or hyper-motility and cardiovascular diseases.

BACKGROUND

The disease diabetes mellitus is characterized by metabolic defects in the production and utilization of carbohydrates which result in the failure to maintain appropriate blood sugar levels. The results of these defects include, inter alia, elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type-1 diabetes, or insulin-dependent diabetes mellitus (IDDM), is the result of an absolute deficiency of insulin, the hormone that regulates carbohydrate utilization. Type-2 diabetes, or non-insulin-dependent diabetes mellitus (NIDDM), often occurs with normal, or even elevated, levels of insulin and appears to be the result of the inability of tissues to respond appropriately to insulin. Most Type-2 diabetic patients are also obese.

Obesity constitutes a major health risk that leads to mortality and incidence of Type-2 diabetes mellitus, hypertension, and dyslipidemia. In the United States, more than 50% of the adult population is overweight, and almost 25% of the population is considered to be obese. The incidence of obesity is increasing in the United States at a three-percent cumulative annual growth rate. While the vast majority of obesity occurs in the United States and Europe, the prevalence of obesity is also increasing in Japan. Furthermore, obesity is a devastating disease which can also wreak havoc on an individual's mental health and self-esteem, which can ultimately affect a person's ability to interact socially with others. Unfortunately, the precise etiology of obesity is complex and poorly understood. In addition, societal stereotypes and presumptions regarding obesity only tend to exacerbate the psychological effects of the disease. Because of the impact of obesity on society in general, much effort has been expended in efforts to treat obesity; however, long-term treatment and/or prevention remains a goal.

β-Adrenergic agents have been generally classified into $\beta_1$, $\beta_2$, and $\beta_3$ receptor-specific subtypes. Agonists of β-receptors promote the activation of adenyl cyclase. Activation of $\beta_1$ receptors invokes an increase in heart rate while activation of $\beta_2$ receptors induces smooth muscle tissue relaxation which produces a drop in blood pressure and the onset of skeletal muscle tremors. Activation of $\beta_3$ receptors is known to stimulate lipolysis (e.g., the breakdown of adipose tissue triglycerides into glycerol and fatty acids) and metabolic rate (energy expenditure), thereby promoting the loss of fat mass. Accordingly, compounds that stimulate $\beta_3$ receptors are useful as anti-obesity agents, and can be further used to increase the content of lean meat in edible animals. In addition, compounds that are $\beta_3$ receptor agonists have hypoglycemic activity; however, the precise mechanism of this effect is presently unknown.

Until recently, $\beta_3$ adrenergic receptors were thought to be found predominantly in adipose tissue; however, $\beta_3$ receptors are now known to be located in such diverse tissues as the intestine, (*J. Clin. Invest.*, 91, 344 (1993)) and the brain (*Eur. J. Pharm.*, 219, 193 (1992)). Stimulation of $\beta_3$ receptors has also been demonstrated to induce relaxation of smooth muscle in the colon, trachea, and bronchi. See, e.g., *Life Sciences*, 44, 1411 (1989); *Br. J. Pharm.*, 112, 55 (1994); and *Br. J. Pharmacol.*, 110, 1311 (1993). Furthermore, stimulation of $\beta_3$ receptors has also been found to induce relaxation of histamine-contracted guinea pig ileum. See, e.g., *J. Pharm. Exp. Ther.*, 260, 1, 192 (1992).

The $\beta_3$ receptor is also expressed in the human prostate (*J. Clin. Invest.*, 91, 344 (1993)). Because stimulation of the $\beta_3$ receptor causes relaxation of smooth muscles that have been shown to express the $\beta_3$ receptor, i.e. intestinal smooth muscle, one of ordinary skill in the art would also predict relaxation of prostate smooth muscle. Therefore, $\beta_3$ agonists are useful in the treatment or prevention of prostate disease.

Commonly assigned U.S. Pat. No. 5,977,124 discloses certain $\beta_3$ adrenergic receptor agonists having utility in the treatment of, inter alia, hypoglycemia and obesity.

U.S. Pat. No. 5,776,983 discloses certain catecholamines as useful $\beta_3$-agonists.

U.S. Pat. No. 5,030,640 discloses the use of certain α-heterocyclic ethanol amino alkyl indoles as growth promoters, bronchodilators, anti-depressants, and anti-obesity agents.

U.S. Pat. No. 5,019,578 discloses certain α-heterocyclic ethanolamines useful as growth promoters.

U.S. Pat. No. 4,478,849 discloses pharmaceutical compositions comprising certain ethanolamine derivatives and methods of using such compositions in the treatment of obesity and/or hyperglycemia.

U.S. Pat. No. 4,358,455 discloses the use of certain heterocyclic compounds of the structural formula Het-CHOH—CH$_2$—NH-aralkyl for treating glaucoma and cardiovascular disease.

European Patent Application Publication No. 0 516 349, published Dec. 2, 1992, discloses certain 2-hydroxyphenethyl amines as possessing anti-obesity, hypoglycemic, and related utilities.

U.S. Pat. No. 5,153,210 discloses the use of certain heterocyclic compounds of the formula R$^0$—X—CH(OH)—CH$_2$—N(R$^1$)—C(R$^2$) (R$^3$)—(CH$_2$)$_n$—Y-A-R$^4$—R$^5$ as anti-obesity and anti-hyperglycemic agents.

PCT International Patent Application Publication No. WO 99/65877, published Dec. 23, 1999, discloses the use of heterocyclic compounds having the structural formula

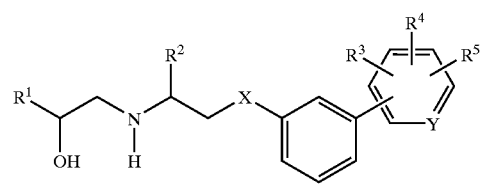

for the treatment of diseases susceptible to amelioration by administration of an atypical beta-adrenoceptor agonist.

SUMMARY

The present invention provides β₃ agonists having Formula (I),

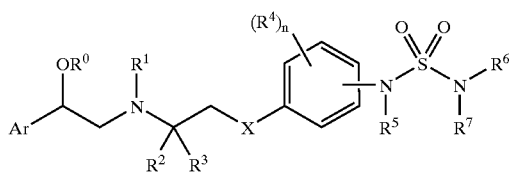

(I)

wherein

Ar is an unsubstituted or substituted aryl, or an unsubstituted or substituted heteroaryl;

$R^0$ is H, hydroxy-protecting group, or taken together with $R^1$ forms a five membered ring;

$R^1$ is H, $(C_1-C_6)$alkyl, amino-protecting group, or taken together with $R^0$ forms a five membered ring;

$R^2$, $R^3$ and $R^5$ are each independently H or $(C_1-C_6)$alkyl;

X is a covalent bond, O, $S(O)_p$, where p is 0, 1 or 2, or $NR^{1a}$, where $R^{1a}$ is H or $(C_1-C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2 or 3; and $R^6$ and $R^7$ are independently H, substituted or unsubstituted $(C_1-C_6)$alkyl, (preferred substituted alkyls include $(C_1-C_3)$ alkyl groups having at least one substituent as defined in the definitions), a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a prodrug thereof; or a pharmaceutically acceptable salt, solvate or hydrate of the compound or the prodrug.

In a preferred embodiment, the compound of Formula (I) is a compound of Formula (IA)

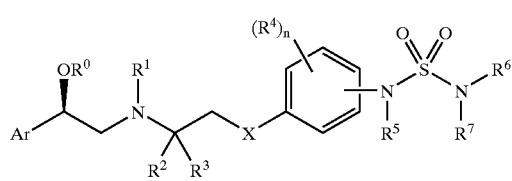

(IA)

where $R^0$, $R^1$, $R^2$, $R^3$, $R^4$, $R^5$, $R^6$, $R^7$, Ar, X and n are as defined above.

In another aspect of the present invention, compounds of Formula (I) where $R^0$ and $R^1$ are hydrogen may be prepared by deprotecting a compound of Formula (II) or Formula (III)

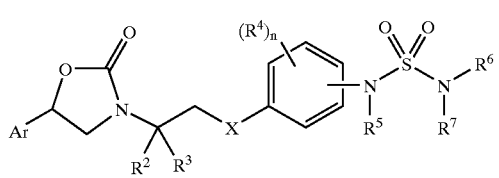

(II)

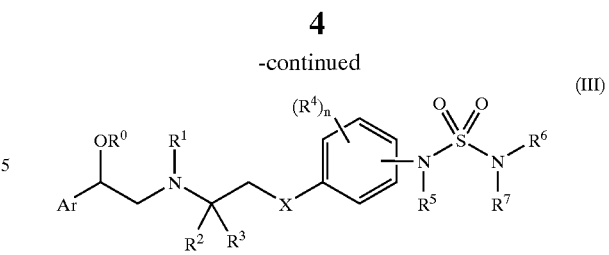

(III)

where $R^0$ is a hydroxy-protecting group; $R^1$ is H or an amino-protecting group; and $R^2$, $R^3$, $R^4$, $R^5$, $R^6$, $R^7$, Ar, X and n are as defined above.

Each of the inventive compounds described herein contain at least one chiral center; consequently, those skilled in the art will appreciate that all stereoisomers (e.g., enantiomers and diastereoisomers) of the compounds disclosed herein are within the scope of the present invention. In addition, tautomeric forms of the compounds are also within the scope of the present invention.

In yet another embodiment of the present invention, a combination is provided that comprises a compound of Formula (I) or (IA) (where $R^0$ and $R^1$ are each independently H or $(C_1-C_6)$ alkyl), a prodrug thereof, or a pharmaceutically acceptable salt, hydrate or solvate of the compound or the prodrug in combination with an anti-obesity agent (e.g., an apo-B/MTP inhibitor, an MCR4 agonist, a CCK-A agonist, a monoamine reuptake inhibitor, a sympathomimetic agent, a serotoninergic agent, a dopamine agonist, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a Neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, a ciliary neurotrophic factor, an AGRP (human agouti-related protein) and the like).

In yet another embodiment of the present invention, a method for treating β₃ adrenergic receptor-mediated diseases, conditions, or disorders in an animal that comprises the step of administering to the animal a therapeutically effective amount of a compound of Formula (I) or (IA) (where $R^0$ and $R^1$ are each independently H or $(C_1-C_6)$ alkyl), a prodrug thereof, or a pharmaceutically acceptable salt, hydrate or solvate of the compound or the prodrug. An anti-obesity agent may also be administered in combination with the compound of the present invention (Formula (I) or (IA) where $R^0$ and $R^1$ are each independently H or $(C_1-C_6)$ alkyl). The compound of the present invention may be administered simultaneously with the anti-obesity agent or separately and in any order.

A compound of the present invention may be administered in the form of a pharmaceutical composition comprising: (1) the compound (Formula (I) or (IA) where $R^0$ and $R^1$ are each independently H or $(C_1-C_6)$ alkyl), a prodrug thereof, or a pharmaceutically acceptable salt, hydrate or solvate of the compound or the prodrug; and (2) a pharmaceutically acceptable carrier, diluent, vehicle or mixture thereof.

The combination therapy may be administered as (a) a single pharmaceutical composition which comprises a compound of the present invention (Formula (I) or (IA) where $R^0$ and $R^1$ are each independently H or $(C_1-C_6)$ alkyl), at least one of the anti-obesity agents described above and a pharmaceutically acceptable excipient, diluent, carrier or mixtures thereof; or (b) two separate pharmaceutical compositions comprising (i) a first composition comprising a compound of the present invention (Formula (I) or (IA) where $R^0$ and $R^1$ are each independently H or $(C_1-C_6)$ alkyl), and a pharmaceutically acceptable excipient, diluent, carrier or mixtures thereof, and (ii) a second composition comprising at least one of the anti-obesity agents described above and a pharmaceutically acceptable excipient, diluent, carrier or mixtures thereof. The pharmaceutical compositions may be administered simultaneously or sequentially and in any order.

In yet another aspect of the present invention, a pharmaceutical kit is provided for use by a consumer to treat or prevent diseases dependent on the signaling pathways associated with β-adrenergic receptors, such as obesity, diabetes, hypertension, gastrointestinal hypo- or hyper-motility and cardiovascular diseases. The kit comprises a) a suitable dosage form comprising a compound of the present invention (Formula (I) or (IA) where $R^0$ and $R^1$ are each independently H or $(C_1-C_6)$ alkyl); and b) instructions describing a method of using the dosage form to treat or prevent $\beta_3$ adrenergic receptor-mediated diseases, conditions, or disorders.

In yet another embodiment of the present invention is a pharmaceutical kit comprising: a) a first dosage form comprising (i) a compound of the present invention (Formula (I) or (IA) where $R^0$ and $R^1$ are each independently H or $(C_1-C_6)$ alkyl), and (ii) a pharmaceutically acceptable carrier, excipient or diluent; b) a second dosage form comprising (i) an anti-obesity agent described above, and (ii) a pharmaceutically acceptable carrier, excipient or diluent; and c) a container.

DEFINITIONS

As used herein, the term "a compound of the present invention" refers to compounds of Formula (I), prodrugs thereof, and pharmaceutically acceptable salts, hydrates and/or solvates of the compounds and/or prodrugs, as well as, all stereoisomers (including diastereomers and enantiomers), tautomers and isotopically labelled compounds.

The term "alkyl" refers to a hydrocarbon radical of the general formula $C_nH_{2n+1}$. The alkane radical may be straight, branched, or cyclic. For example, the term "$(C_1-C_6)$alkyl" refers to a monovalent, straight, branched, or cyclic aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, 1,1-dimethylpropyl, neopentyl, 3,3-dimethylpropyl, cyclopentyl, n-hexyl, 2-methylpentyl, 2-ethylbutyl, 3-methylpentyl, 3-ethylbutyl, 4-methylpentyl, and other constitutional isomers containing 1 to 6 carbon atoms (including stereoisomers). The alkane radical may be unsubstituted or substituted with one or more substituents. For example, a "haloalkyl" refers to an alkyl group substituted with one or more halogen atoms (e.g., fluoromethyl, difluoromethyl, trifluoromethyl, perfluoroethyl, and the like). Similarly, the alkyl portion of an alkoxy, alkylamino, dialkylamino, or alkylthio group have the same definition as above.

The term "partially saturated or fully saturated cycloalkyl" or "partially saturated or fully saturated heterocyclic ring" refers to nonaromatic rings that are either partially or fully hydrogenated. For example, partially or fully saturated cycloalkyl includes groups such as cyclopropyl, cyclopropenyl, cyclobutyl, cyclobutenyl, cyclopentyl, cyclopentenyl, cyclopentadienyl, cyclohexyl, cyclohexenyl, cyclohexadienyl, and the like. Partially saturated or fully saturated heterocyclic rings include groups such as dihydropyridinyl, pyrrolidinyl, (2-, 3- or 4-)-N-methylpyrrolidinyl, piperidinyl, piperazinyl, pyrazolidyl, imidazolyl, imidazolidyl, 2H-pyranyl, 4H-pyranyl, 2H-chromenyl, morpholino, thiomorpholino, tetrahydrothienyl and the like. The cycloalkyl and heterocyclic rings may be unsubstituted or substituted. The substituents may be independent substitutions on the ring or form a fused, a bridging (e.g., bicyclo[2.2.1]heptyl), or a spiral ring system. The fused ring may be aromatic or non-aromatic. The additional ring system may contain one or more heteroatoms (preferably no more than three). For example, the term "spirocycloalkyl" means a cycloalkyl ring having a spiro union (the union formed by a single atom which is the only common member of the rings). In addition, it is understood that, unless specifically noted otherwise, all suitable isomers of the cyclic ring groups are included herein.

Exemplary rings consisting of two fused partially saturated, fully saturated, or fully unsaturated five- and/or six-membered rings, taken independently, optionally having one to four heteroatoms are anthranilyl, benzimidazolyl, benzofuryl, 2H-1-benzopyranyl, benzothiazolyl, benzo[b]thienyl, benzo[c]thienyl, 2H-1,3-benzoxazinyl, 2H-1,4-benzoxazinyl, 1H-2,3-benzoxazinyl, 4H-3,1-benzoxazinyl, 2H-1,2-benzoxazinyl, 4H-1,4-benzoxazinyl, benzoxazolyl, cinnolinyl, cyclopenta[b]pyridinyl, decalinyl, indazolyl, indenyl, indolinyl, indolizinyl, indolyl, 1H-indoxazinyl, isobenzofuryl, isoindenyl, isoindolyl, isoquinolinyl, naphthyl, naphthyridinyl, phthalazinyl, 1,8-pteridinyl, purinyl, pyrano[3,4-b]pyrrolyl, pyrido[3,2-b]-pyridinyl, pyrido[3,4-b]-pyridinyl, pyrido[4,3-b]-pyridinyl, quinazolinyl, quinolinyl, quinoxalinyl, and tetralinyl.

The term "alkenyl" refers to a hydrocarbon containing at least one carbon-carbon double bond. As described above for alkyl, the alkene radical may be straight or branched and the alkene radical may be unsubstituted or substituted with one or more substituents.

The term "aryl" refers to aromatic moieties having single (e.g., phenyl) or fused ring systems (e.g., naphthalene, anthracene, phenanthrene, etc.). The aryl groups may be unsubstituted or substituted with one or more substituents (preferably no more than three substituents). Substituted aryl groups include a chain of aromatic moieties (e.g., biphenyl, terphenyl, phenylnaphthalyl, etc.)

The term "heteroaryl" refers to aromatic moieties containing at least one heteratom (e.g., oxygen, sulfur, nitrogen or combination thereof) within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be unsubstituted or substituted with one or more substituents (preferably no more than three substituents).

Representative examples of five- and six-membered aromatic or non-aromatic heterocyclic groups include chromenyl, dihydropyridazinonyl, dihydropyridazinyl, furyl, imidazolidinyl, imidazolyl, indazolyl, indolizinyl, indolyl, isobenzofuranyl, isoindolyl, isoquinolyl, isothiazolyl, isoxazolyl, morpholinyl, naphthyridinyl, oxadiazolyl, oxazinyl, oxazolinyl, oxazolyl, phthalazinyl, piperazinyl, piperidinyl, purinyl, pyranyl, pyrazolyl, pyridazinonyl, pyridazinyl, pyridyl, pyrimidinonyl, pyrimidyl, pyrrolidinyl, pyrrolyl, quinolizinyl, quinolyl, quinoxalinyl, thiadiazolyl, thiazolinyl, thiazolyl, thienyl, thiomorpholinyl, triazolyl, and xanthenyl. It is to be understood that the heterocyclic radical may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

Specific representative examples of five- to six-membered aromatic or non-aromatic heterocyclic groups include 1,4-dioxanyl, 3H-1,2,3-dioxazolyl, 1,2,4-dioxazolyl, 1,3,2-dioxazolyl, 1,3,4-dioxazolyl, 1,2-dioxinyl, 1,3-dioxinyl, 1,3-dioxolanyl, 1,4-dithianyl, 1,2-dithiolyl, 1,3-dithiolyl, 2-imidazolinyl, 2H-imidazolyl, o-isoxazinyl, p-isoxazinyl, 1,2,3-oxadiazolyl, 1,2,4-oxadiazolyl, 1,2,5-oxadiazolyl, 1,3,4-oxadiazolyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, 1,2,5-oxathiazinyl, 1,2,6-oxathiazinyl, 1,4,2-oxadiazinyl, 5H-1,2,5-oxathiazolyl, 3H-1,2-oxathiolyl, 1,3-oxathiolyl, 2H-pyranyl, 4H-pyranyl, 2-pyrazolinyl, 2-pyrrolinyl, 3-pyrrolinyl, 1,3,4-thiadiazolyl, 1,2,3-triazinyl, 1,2,4-triazinyl, 1,3,5-triazinyl, 1,2,3-triazolyl, 1,2,4-triazolyl, and 1,3,5-trithianyl.

The term "substituted" means that a hydrogen atom on a molecule has been replaced with a different atom or molecule. The atom or molecule replacing the hydrogen atom is denoted as a "substituent." The term substituted specifically envisions and allows for substitutions which are common in the art. However, it is generally understood by those skilled in the art that the substituents should be selected so as to not adversely affect the pharmacological characteristics of the compound or adversely interfere with the use of the medicament. Suitable substituents for any of the groups defined above for the compound of Formula (I) include $(C_1-C_6)$ alkyl, $(C_1-C_6)$alkenyl, $(C_3-C_6)$cycloalkyl, $(C_3-C_6)$ heterocycloalkyl (e.g., tetrahydrofuryl), aryl, heteroaryl, halo (e.g., chloro, bromo, iodo and fluoro), cyano, hydroxy, $(C_1-C_6)$alkoxy, aryloxy, sulfhydryl (mercapto), $(C_1-C_6)$ alkylthio, arylthio, mono- and di-$(C_1-C_6)$alkyl amino, quaternary ammonium salts, amino$(C_1-C_6)$alkoxy, hydroxy $(C_1-C_6)$alkylamino, amino$(C_1-C_6)$alkylthio, cyanoamino, nitro, carbamyl, keto (oxy), carbonyl, carboxy, glycolyl, glycyl, hydrazino, guanyl, sulfamyl, sulfonyl, sulfinyl, thiocarbonyl, thiocarboxy, and combinations thereof.

The term "protecting group" or "Pg" refers to a substitutent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl (e.g., t-butyl-dimethylsilyl). A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis,* John Wiley & Sons, New York, 1991.

The phrase "therapeutically effective amount" means an amount of a compound of the present invention that attenuates, ameliorates, or eliminates a particular disease, condition, or disorder, or prevents or delays the onset of a particular disease, condition, or disorder.

The term "animal" refers to humans, companion animals (e.g., dogs, cats and horses), food-source animals (i.e., edible animals such as cows, pigs, sheep and poultry), zoo animals, marine animals, birds and other similar animal species. Preferred animals are humans.

The phrase "pharmaceutically acceptable" indicates that the substance or composition must be compatible chemically and/or toxicologically, with the other ingredients comprising a composition, and/or the animal being treated therewith.

The terms "treating", "treat", or "treatment" embrace both preventative, i.e., prophylactic, and palliative treatment.

DETAILED DESCRIPTION

The present invention provides $\beta_3$ adrenergic receptor agonists (as well as amino- and hydroxy-protected intermediate precursors) having structural Formula (I),

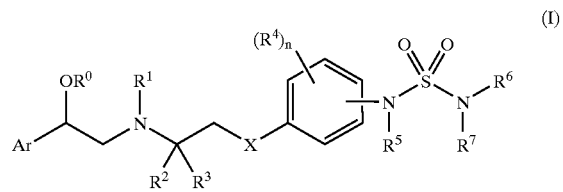

(I)

wherein $R^0$, $R^1$, $R^2$, $R^3$, $R^4$, $R^5$, $R^6$, $R^7$, Ar, n and X have the meanings set forth above.

Preferred compounds of the present invention are those that exist in the (R)-stereoconfiguration, designated by Formula (IA) hereinbelow.

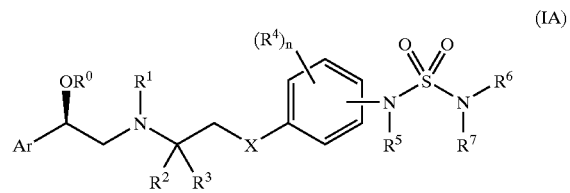

(IA)

Compounds of Formula (I) or (IA) where n is 0, and $R^1$ and $R^5$ are hydrogen are preferred. Compounds of Formula (I) or (IA) where Ar is pyridyl (in particular, 3-pyridyl) or a substituted phenyl (in particular, 3-chlorophenyl) are also preferred. Preferred substituents for $R^2$ and $R^3$ in both the compounds of Formula (I) and (IA) are hydrogen or methyl. Substituent X is preferably a covalent bond or an oxygen. Preferred substitutents for $R^6$ and $R^7$ are independently H, substituted or unsubstituted $(C_1-C_6)$alkyl, substituted or unsubstituted $(C_3-C_6)$cycloalkyl, or taken together form a substituted or unsubstituted, heterocyclic 4 to 7 membered ring.

Compounds of Formula (I) may be synthesized in vitro using laboratory techniques, such as those well known to the synthetic organic chemist of ordinary skill, or synthesized using in vivo techniques, such as through metabolism, fermentation, digestion, and the like. In addition, the compounds of Formula (I) may be synthesized using a combination of in vitro and in vivo techniques. The preferred method for synthesizing compounds of the present invention is by synthetic routes that include processes analogous to those known in the chemical arts, particularly in light of the description contained herein.

For illustrative purposes, the reaction schemes depicted below provide potential routes for synthesizing the inventive compounds as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions.

Scheme I

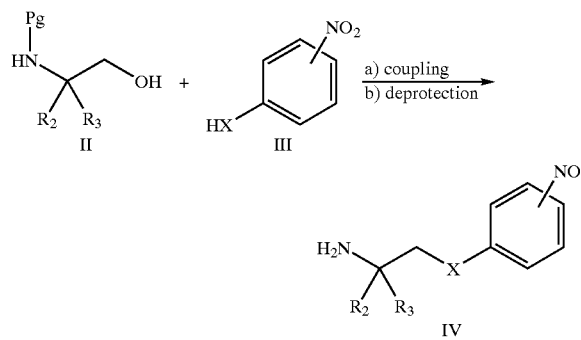

Scheme I illustrates the preparation of intermediate IV which is used as the starting material for synthesizing compounds of Formula (I) in Schemes II and IV below. The preparation of intermediate IV is described in U.S. Pat. No. 5,977,124 and incorporated herein by reference. In general, the (protected) amino alcohol II, where Pg is an amino-protecting group, is first dehydratively coupled with compound III to make the (protected) amino intermediate IV. Suitable compounds of formula III include o-, m- or p-nitrophenols, o-, m- or p-nitrophenylthiols, o-, m- or p-nitroaminobenzenes and derivatives thereof having one to three substitutions (e.g., substituted and unsubstituted ($C_1$–$C_6$) alkyl, cyano, substituted and unsubstituted ($C_1$–$C_6$) alkyoxy groups or combinations thereof). The phenylnitro compounds are generally available from a variety of commercial suppliers well known to those skilled in the art or may be prepared from commercially available materials using conventional procedures well known to those skilled in the art. Suitable amino-protecting groups (Pg) include acetyl, trifluoroacetyl, t-butoxycarbonyl (BOC), benzyloxycarbonyl (CBz) and 9-fluorenylmethylenoxycarbonyl (Fmoc). The reaction is typically run with stirring at room temperature (or higher, if preferred) in the presence of a dehydrating agent. A suitable dehydrating agent is a stoichiometric amount of diethylazodicarboxylate and a phosphine (e.g., triphenylphosphine). The reaction may be run in any inert solvent. Suitable inert solvents include tetrahydrofuran (THF), benzene, toluene, halogenated hydrocarbons (e.g., dichloroethane, chloroform, or methylene chloride), dimethylformamide (DMF), or dimethylsulfoxide (DMSO). The (protected) amino intermediate IV can then be deprotected using standard chemistry well know to those skilled in the art. For example, the protecting group may be removed by treatment with an inorganic acid (e.g., HCl) or organic acid (e.g., trifluoroacetic acid (TFA)) in an inert solvent (e.g., chloroform or methylene chloride) at room temperature for about 2 to about 8 hours. Alternatively, the protecting group may be removed by hydrogenolysis using hydrogen in the presence of a palladium-on-carbon catalyst in an inert solvent (e.g., lower alcohol or DMF). The hydrogenolysis is typically run at a temperature between about 20° C. to about 90° C.

Scheme II below illustrates one potential route for synthesizing compounds of Formula (I) and is exemplified in Example 1 of the Examples section.

Scheme II

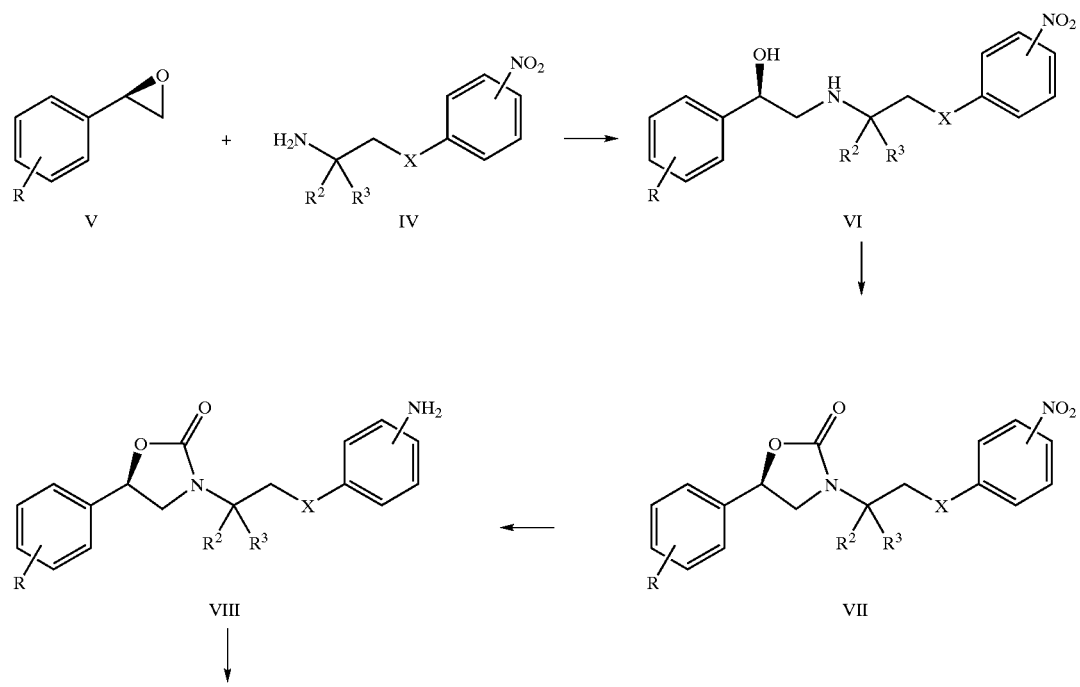

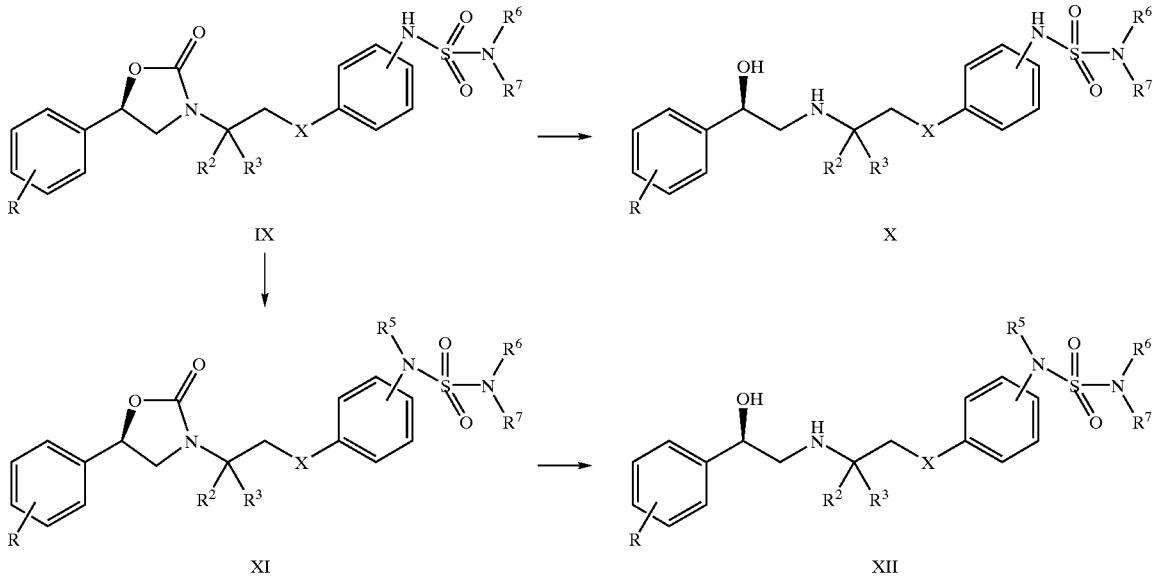

Amine IV is converted to the corresponding N-trimethylsilyl derivative by treatment with a silylating reagent (preferably N-trimethylsilylacetamide) in an inert reaction solvent (e.g., DMSO, DMF, toluene, THF and the like) for about 15 minutes to about 3 hours at room temperature. Epoxide V is then added and the reaction is stirred at about 50° C. to about 150° C., preferably about 100° C., for a time period from about 8 to about 48 hours, depending on the particular substitutents for $R^2$ and $R^3$, to provide the hydroxy compound VI. A solution of VI in an inert reaction solvent (e.g., THF, dichloromethane, etc) is treated with 1,1-carbonyldiimidazole at about 0° C. to about 60° C., preferably at or near room temperature (RT) for about 1 to about 12 hours, preferably about 6 hours. The nitro compound VII is reduced to the amino compound VIII using reducing conditions well known to those skilled in the art. For example, the reduction may be accomplished using stannous chloride in a protic solvent (preferably in ethanol) at or near RT to about 100° C. (preferably about 70° C.) for about 2 to about 12 hours (preferably about 6 hours). Alternatively, the reduction may be accomplished using a hydrogen source such as ammonium formate or hydrogen gas and a catalyst, preferably 10% palladium-on-carbon in a protic solvent (preferably methanol) at about 0° C. to about 100° C. (preferably about 60° C.).

Compound VIII is then treated with an appropriate sulfamoyl chloride (i.e., a sulfamoyl chloride containing the desired $R^6$ and $R^7$ substituents or substitutents that can be converted into the desired $R^6$ and $R^7$ substitutents) and a base (e.g., triethylamine) in an aprotic solvent (e.g., 1,2-dichloroethane) at or near RT to about 100° C. (preferably about 60° C. to about 70° C.) for about 8 to about 48 hours (preferably about 18 hours). Suitable sulfamoyl chlorides include N-piperidinylsulfamoyl chloride, N,N-dimethylsulfamoyl chloride, N-cyclohexylsulfamoyl chloride, N-(cyclohexylmethyl)sulfamoyl chloride, N-cyclohexyl-N-methylsulfamoyl chloride, N-cyclopropylsulfamoyl chloride, N-(cyclopropylmethyl) sulfamoyl chloride, N-(1,1-dimethyl-2-phenylethyl) sulfamoyl chloride, N-[(2R,6S)-2,6-dimethyl-4-morpholinyl]sulfamoyl chloride, N-[4-methyl-1-piperidinyl]sulfamoyl chloride, N-[(3R,5S)-3,5-dimethyl-1-piperidinyl]sulfamoyl chloride, N-[4-phenyl-1-piperidinyl] sulfamoyl chloride, N-[(1S)-1-phenylethyl]sulfamoyl chloride, N-(octahydro-(4aR,8aR)-2(1H)-isoquinolinyl) sulfamoyl chloride, N-phenylsulfamoyl chloride, N-(3-methyl-3-phenyl-1-piperidinyl)sulfamoyl chloride, N-(3,3-dimethyl-1-piperidinyl)sulfamoyl chloride, N-(2,3-dihydrospiro[1H-indene-1,3'-piperidinyl])sulfamoyl chloride, N-[(1R,2S)-2-phenylcyclopropyl]sulfamoyl chloride, N-(2, 3-dihydro-1H-inden-1-yl)sulfamoyl chloride, N-[(1R,2S, 4S)-endo-bicyclo[2.2.1]hept-2-yl]sulfamoyl chloride, N-(2-methoxyethyl)sulfamoyl chloride, N-[((2S)-tetrahydro-2-furanyl)methyl]sulfamoyl chloride, N-(4-methyl-1-piperazinyl)sulfamoyl chloride, N-(4-phenylmethyl-1-piperazinyl)sulfamoyl chloride, N-cyclobutylsulfamoyl chloride, N-piperazinylsulfamoyl chloride, N-[1-(phenylmethyl)-4-piperidinyl]sulfamoyl chloride, N-[(3S)-1-(phenylmethyl)-3-pyrrolidinyl]sulfamoyl chloride, N-[(1S,2S)-2-(phenylmethoxy)cyclopentyl]-sulfamoyl chloride, N-hexahydro-1H-azepinylsulfamoyl chloride, N-methyl-N-(2-phenylethyl)sulfamoyl chloride, N-methyl-N-isopropylsulfamoyl chloride, N-[3,4-dihydro-2(1H)-isoquinolinyl]sulfamoyl chloride, N-[2(2S)-methoxymethyl)1-pyrrolidinyl]sulfamoyl chloride, N-(2,3-dihydro-1H-inden-2-yl)sulfamoyl chloride, N-methyl-N-phenylsulfamoyl chloride, N-(4-tert-butyl-1-piperidinyl) sulfamoyl chloride, N-(octahydro-(4aS,8aS)-2(1H)-isoquinolinyl)sulfamoyl chloride, N-(3-cyclohexyl-1-piperidinyl)sulfamoyl chloride, N-(4-cyano-4-phenyl-1-piperidinyl)sulfamoyl chloride, N-[3-(4-methoxyphenyl) methyl-1-pyrrolidinyl]sulfamoyl chloride, N-[5-methoxy-3, 4-dihydro-spiro-1(2H)naphthalyl-4-piperidinyl]sulfamoyl chloride, N-[1-(4-methylphenyl)-3-azabicyclo[3.1.0]hex-3-yl]sulfamoyl chloride, and N-[7-(trifluoromethyl)-1,2,4,5-tetrahydro-1,5-methano-3H-3-benzazepin-3-yl]sulfamoyl chloride. Compound IX is then treated with an inorganic base (preferably potassium hydroxide) in a protic solvent (preferably ethanol) at about 50° C. to about 100° C. (preferably about 80° C.) for about 5 to about 48 hours (preferably 24 hours) to provide the deprotected compound X (a compound of the present invention where $R^5$ is hydrogen).

Alternatively, compound IX is treated with a base (preferably lithium bis(trimethylsilyl)amide) at about 0° C.

to about −78° C. (preferably about 0° C.) for about 1 to about 3 hours in an aprotic solvent (preferably DMF) followed by treatment with an alkyl (i.e., $R^5$) halide at about 0° C. to about 50° C. (preferably at or near RT) for about 1 to about 12 hours (preferably about 8 hours). Suitable alkyl halides include any ($C_1$–$C_6$) alkyl halide, where the halide portion may be a chloride, bromide or iodide and suitable ($C_1$–$C_6$) alkyl groups include methyl, ethyl, n-propyl, iso-propyl, n-butyl, iso-butyl, sec-butyl, tert-butyl, cyclopropylmethyl, cyclobutyl, n-pentyl, 1-methylbutyl, 2-methylbutyl, 3-methylbutyl, 1,1-dimethylpropyl, neopentyl, 3,3-dimethylpropyl, cyclopentyl, hexyl, 2-methylpentyl, 2-ethylbutyl, 3-methylpentyl, 3-ethylbutyl, 4-methylpentyl, cyclpentylmethyl, 3-cyclopropylpropyl, 2-cyclobutylethyl, cyclohexyl and other constitutional isomers. Preferred alkyl halides are methyl iodide and methyl bromide. Compound XI is then deprotected by treatment with an inorganic base (preferably potassium hydroxide) in a protic solvent (preferably ethanol) at about 50° C. to about 100° C. (preferably about 80° C.) for about 5 to about 48 hours (preferably 24 hours) to provide compound XII (a compound of the present invention where $R^5$ is a ($C_1$–$C_6$)alkyl group).

Scheme III illustrates the preparation of intermediate XVII which is used as a starting material for the synthesis of compounds of Formula (I) according the synthetic routes depicted in Schemes IV and V. Although a specific aromatic material (XIII) is used in Scheme III, one skilled in the art will appreciate that other aromatic compounds can be easily substituted for the pyridine derivative (XIII) to produce other aromatic intermediates. The synthetic route illustrated in Scheme III is further exemplified in the preparations section of the Examples.

minutes (preferably about 30 minutes). The resultant intermediate is then hydrolyzed with an acid or base (preferably methanol and sulfuric acid). The reaction mixture is warmed to room temperature and allowed to stir for an additional time period from about 30 minutes to about 90 minutes (preferably about 1 hour).

The resultant 2-chloro-5-formylpyridine compound (XIII) is converted to the corresponding 2-chloro-5-vinylpyridine compound (XIV) by reacting XIII with a methylating reagent (preferably prepared from methyltriphenyl-phosphonium bromide and potassium tert-butoxide) in the presence of a polar aprotic solvent (e.g., tetrahydrofuran (THF)). The resulting reaction mixture is stirred for about 15 minutes to about 45 minutes (preferably about 30 minutes) at a temperature from about −40° C. to about 50° C. (preferably about 5° C.).

The 2-chloro-5-vinylpyridine compound (XIV) is converted to the corresponding diol compound (XV) by reacting XIV with a dihydroxylating agent (e.g., osmium tetroxide or potassium permanganate, preferably osmium tetroxide) with or without a co-oxidant (e.g., potassium ferricyanide, hydrogen peroxide, t-butyl hydroperoxide or N-methylmorpholine-N-oxide, preferably potassium ferricyanide) in the presence of t-butanol and water. The oxidation can be performed in the presence of a coordinating ligand (e.g., hydroquinidine 1,4-phthalazinediyl diether or hydroquinine 1,4-phthalazinediyl diether) which affords the enantiomerically enriched diol. The reaction mixture is stirred at a temperature from about −30° C. to about 10° C. (preferably about 5° C.) for about 4 hours to about 18 hours (preferably about 6 hours).

The diol compound (XV) is converted to the corresponding compound of formula XVI by reacting the diol XV with

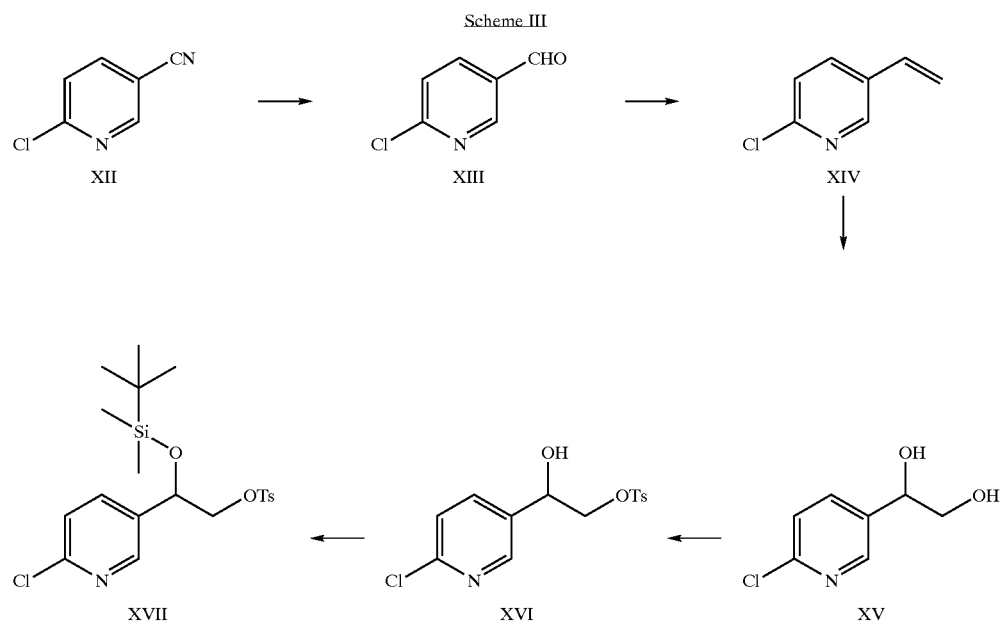

Scheme III

In Scheme III above, the 2-chloro-5-cyanopyridine compound (XII) is converted to the corresponding 2-chloro-5-formylpyridine compound (XIII) by reacting XII with a reducing agent (e.g., diisobutylaluminum hydride) in the presence of an aprotic solvent (e.g., toluene). The reaction is stirred at a temperature between about 0° C. to about 10° C. (preferably about 5° C.) for about 15 minutes to about 45 the appropriate sulfonylchloride (e.g., p-toluenesulfonyl chloride (TsCl), methanesulfonyl chloride, m-nitrobenzenesulfonyl chloride, p-nitrobenzenesulfonyl chloride or benzenesulfonyl chloride, preferably p-toluenesulfonyl chloride) in the presence of a base. Suitable bases include lower trialkylamines, pyridine and pyridine derivatives. Preferred bases include triethylamine, diisopropylethylamine, pyridine, 2,4,6-collidine and 2,6-lutidine. Pyridine is the most preferred base. It is preferred that the solvent is a polar solvent such as ethers (e.g., tetrahydrofuran, dioxane and dimethoxyethane), aromatic hydrocarbons (e.g., toluene and xylene), chlorinated hydrocarbons (e.g., carbon tetrachloride, chloroform and methylene chloride), dimethylformamide, N-methyl-2-pyrrolidinone, dimethylacetamide, pyridine, or mixtures thereof. The reaction mixture is stirred at a temperature from about 0° C. to about 10° C. (preferably 5° C.) for about 6 hours to about 24 hours (preferably about 12 hours).

Compound XVI is converted to the corresponding compound XVII by reacting XVI with a silyating agent such as a trialkylchlorosilane (e.g., t-butyldimethylsilyl chloride, triethylchlorosilane, and triisopropylchlorosilane), or a alkylarylchlorosilane (e.g., diphenylmethylchlorosilane) in the presence of a base and a polar protic solvent. A preferred silyating agent is t-butyldimethylsilyl chloride. Suitable bases include triethylamine, N,N-diisopropylethylamine, imidazole, pyridine, 2,6-lutidine and N-methylmorpholine. A preferred base is imidazole. Suitable polar protic solvents include dimethylacetamide, tetrahydrofuran (THF), dimethylformamide (DMF), methylene chloride and chloroform. A preferred solvent is dimethylformamide. The reaction is carried out at a temperature from about 0° C. to about 10° C. (preferably about 5° C.) and then warmed to room temperature over a time period from about 14 hours to about 22 hours (preferably about 18 hours.)

Scheme IV illustrates another synthetic route for the synthesis of compounds of Formula (I) and is further exemplified in Example 2 of the Examples.

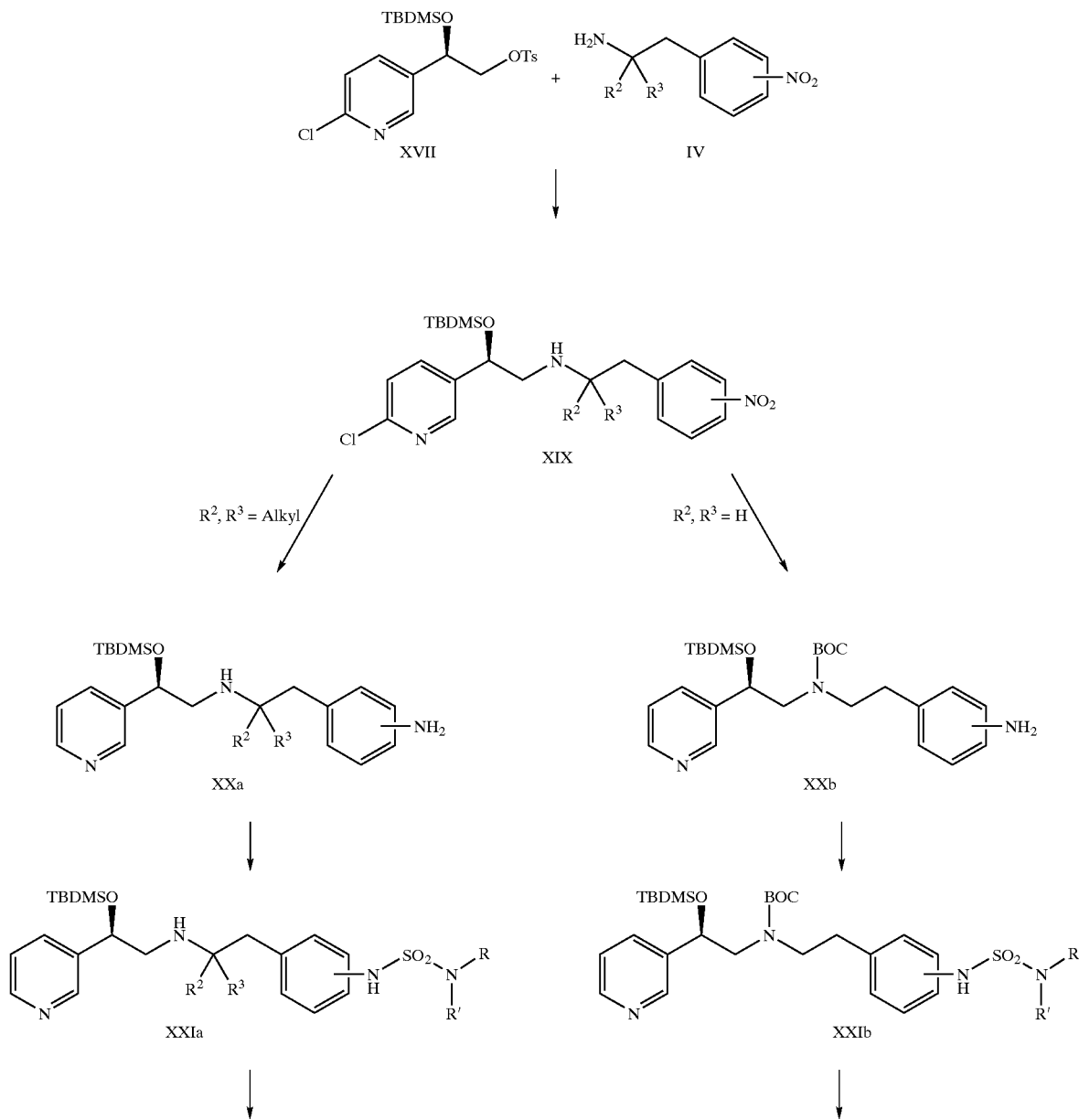

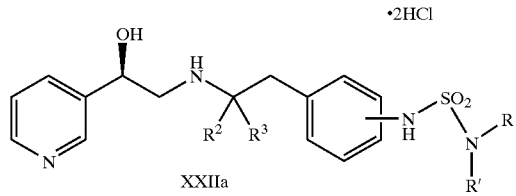

XXIIa

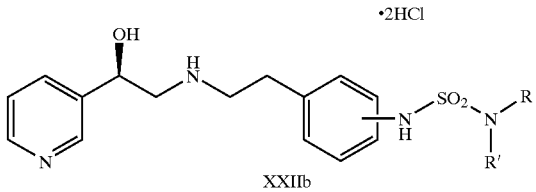

XXIIb

In Scheme IV above, compound XVII is converted to the corresponding compound of formula XIX by reacting XVII with an amine of formula IV in the presence of N,N-diisopropylethylamine and a polar aprotic solvent (e.g., dimethylsulfoxide (DMSO)). The reaction is stirred at a temperature from about 70° C. to about 90° C. (preferably about 80° C.) for about 5 hours to about 9 hours (preferably about 7 hours). Compound XIX is converted to compound XXIa using procedures analogous to those described in Scheme II for the conversion of compound VII to compound IX (reduction of the nitro group to an amino group followed by coupling of the amine with the desired sulfamoyl chloride). Compound XXIa is treated with tetra-n-butylammonium fluoride in the presence of an aprotic solvent (e.g., THF). The reaction is stirred at or near room temperature for about 3 hours to about 12 hours (preferably about 8 hours). A solution (preferably in methanol) of the resultant intermediate is then treated with a solution of hydrogen chloride (e.g., 4N HCl in 1,4-dioxane) for about 15 minutes to about 2 hours (preferably about 0.5 hr) at about 0° C. to about 50° C. (preferably at or near RT) to produce compound XXIIa (a compound of the present invention where $R^2$ and $R^3$ are independently $(C_1-C_6)$alkyl).

Alternatively, a compound XIX, where $R^2$ and $R^3$ are both hydrogen, is converted to a compound of the present invention, where $R^2$ and $R^3$ are both hydrogen, using the following procedure. Compound XXb is prepared via a two-step process involving protection of the secondary amine (preferably as a carbamate) by treatment with an acylating agent (preferably di-t-butyl dicarbonate) in an aprotic solvent (e.g., THF) at about 0° C. to about 50° C. (preferably at or near RT). The nitro group of the resultant intermediate is then reduced to the corresponding amino compound XXb followed by coupling of the amine with the desired sulfamoyl chloride to produce compound XXIIb using procedures analogous to the conversion of compound VII to IX in Scheme II above. XXIIb is then prepared using procedures analogous to those described for the preparation of XXIIa above.

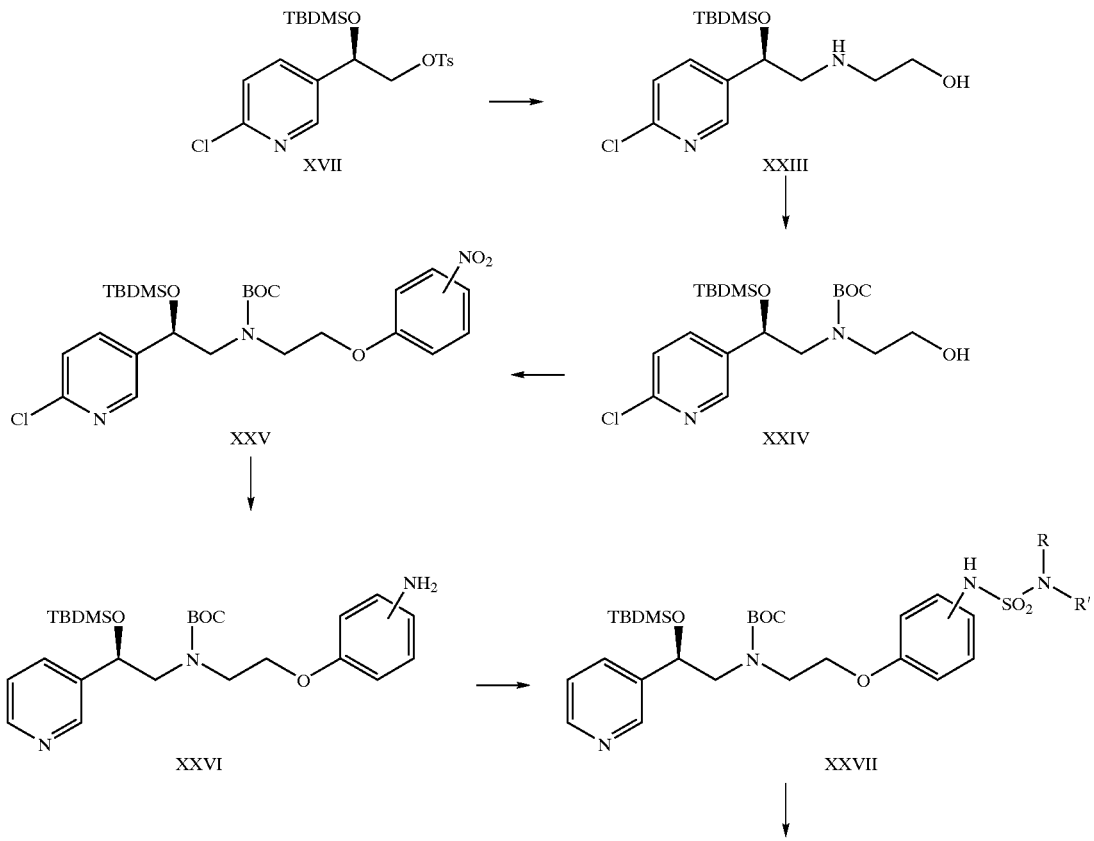

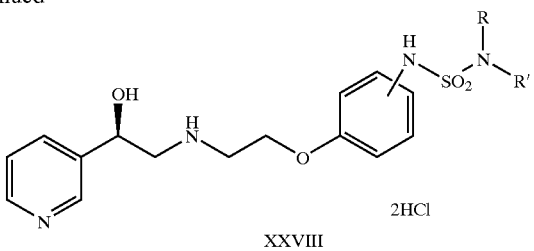

XXVIII · 2HCl

Compounds of the present invention where X is oxygen may alternatively be prepared using the general procedures outlined in Scheme V. Compound XVII is converted to the corresponding compound of formula XXIII by reacting XVII with ethanolamine in the presence of N,N-diisopropylethylamine and a polar aprotic solvent (e.g., dimethylsulfoxide (DMSO)). The reaction is stirred at a temperature from about 70° C. to about 90° C. (preferably about 80° C.) for about 5 hours to about 9 hours (preferably about 7 hours).

A protecting group is attached to the secondary amino group of XXIII by treating XXIII with an acylating agent (preferably di-t-butyl dicarbonate) in an aprotic solvent (e.g., THF) at about 0° C. to about 50° C. (preferably at or near RT). Analogous to the coupling reaction described earlier in Scheme I, the (protected) amino alcohol XXIV is dehydratively coupled with 4-nitrophenol (preferably in the presence of a stoichiometric amount of diethylazodicarboxylate and triphenylphosphine).

Compound XXV is converted to compound XXVII using procedures analogous to those described in Scheme II for the conversion of compound VII to compound IX (reduction of the nitro group to an amino group followed by coupling of the amine with the desired sulfamoyl chloride). Compound XXVII is treated with tetra-n-butylammonium fluoride in the presence of an aprotic solvent (e.g., THF). The reaction is stirred at or near room temperature for about 3 hours to about 12 hours (preferably about 8 hours). A solution (preferably in methanol) of the resultant intermediate is then treated with a solution of hydrogen chloride (e.g., 4N HCl in 1,4-dioxane) for about 15 minutes to about 2 hours (preferably about 0.5 hr) at about 0° C. to about 50° C. (preferably at or near RT) to produce compound XXVIII as its hydrogen chloride salt.

For those compounds of the present invention where X is a covalent bond, the starting p-nitrophenethylamine is available from commercial sources or can be prepared by one skilled in the art using conventional chemistry from commerically available materials. Compounds of the present invention where X is a sulfone (SO) or sulfoxide ($SO_2$) can be prepared from the corresponding sulfide (described earlier) by conventional oxidation chemistry well known to those skilled in the art (e.g., oxidation with peroxides, such as hydrogen peroxide, m-chloroperbenzoic acid and the like).

Conventional methods and/or techniques of separation and purification known to one of ordinary skill in the art can be used to isolate the compounds of Formula (I), as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of their pharmaceutically acceptable salts, solvates and/or hydrates. The term "salts" refers to inorganic and organic salts of a compound of the present invention. These salts can be prepared in situ during the final isolation and purification of a compound, or by separately reacting the compound or prodrug with a suitable organic or inorganic acid and isolating the salt thus formed. Representative salts include the hydrobromide, hydrochloride, sulfate, bisulfate, nitrate, acetate, oxalate, besylate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, Berge, et al., J. Pharm. Sci., 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) contains a carboxylic acid functional group, a prodrug can comprise an ester formed by the replacement of the hydrogen atom of the acid group with a group such as ($C_1$–$C_8$)alkyl, ($C_2$–$C_{12}$) alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a compound of Formula (I) contains an alcohol functional group, a prodrug can be formed by the replacement of the hydrogen atom of the alcohol group with a group such as ($C_1$–$C_6$)alkanoyloxymethyl, 1-(($C_1$–$C_6$) alkanoyloxy)ethyl, 1-methyl-1-(($C_1$–$C_6$)alkanoyloxy)ethyl, ($C_1$–$C_6$)alkoxycarbonyloxymethyl, N-($C_1$–$C_6$)

alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)alkyl)_2$ or glycosyl (the radical resulting from the removal of a hydroxyl group of the hemiacetal form of a carbohydrate).

If a compound of Formula (I) incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl-natural α-aminoacyl, $—C(OH)C(O)$ OY wherein Y is H, $(C_1-C_6)$alkyl or benzyl, $—C(OY_0)Y_1$ wherein $Y_0$ is $(C_1-C_4)$ alkyl and $Y_1$ is $(C_1-C_6)$alkyl, carboxy $(C_1-C_6)$alkyl, amino$(C_1-C_4)$alkyl or mono-N- or di-N,N-$(C_1-C_6)$alkylaminoalkyl, $—C(Y_2)Y_3$ wherein $Y_2$ is H or methyl and $Y_3$ is mono-N- or di-N,N-$(C_1-C_6)$alkylamino, morpholino, piperidin-1-yl or pyrrolidin-1-yl.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond, both the cis- and trans-forms, as well as mixtures, are embraced within the scope of the invention.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

The compounds of Formula (I) may exist in unsolvated as well as solvated forms with pharmaceutically acceptable solvents such as water, ethanol, and the like, and it is intended that the invention embrace both solvated and unsolvated forms.

It is also possible that the compounds of Formula (I) may exist in different tautomeric forms, and all such forms are embraced within the scope of the invention. For example, all of the tautomeric forms of the imidazole moiety are included in the invention. Also, for example, all keto-enol and imine-enamine forms of the compounds are included in the invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by carrying out the procedures analogous to those disclosed in the Schemes and/or in the Examples hereinbelow, by substituting an isotopically labelled reagent for a non-isotopically labelled reagent.

In another aspect of the instant invention, the compounds of Formula (I) or (IA), or prodrugs thereof (including the pharmaceutically acceptable salts, hydrates or solvates of the compounds and prodrugs) can be employed in combination with an anti-obesity agent.

The anti-obesity agent is preferably selected from the group consisting of an apolipoprotein-B secretion/ microsomal triglyceride transfer protein (apo-B/MTP) inhibitor, an MCR-4 agonist, a cholecystokinin-A (CCK-A) agonist, a monoamine reuptake inhibitor (such as sibutramine), a sympathomimetic agent, a serotoninergic agent, a dopamine agonist (such as bromocriptine), a melanocyte-stimulating hormone receptor analog, a cannabinoid receptor antagonist, a melanin concentrating hormone antagonist, leptin (the OB protein), a leptin analog, a leptin receptor agonist, a galanin antagonist, a lipase inhibitor (such as tetrahydrolipstatin, i.e. orlistat), an anorectic agent (such as a bombesin agonist), a Neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, a ciliary neurotrophic factor (such as Axokine™ available from Regeneron Pharmaceuticals, Inc., Tarrytown, N.Y. and Procter & Gamble Company, Cincinnati, Ohio), and human agouti-related protein (AGRP). Other anti-obesity agents, including the preferred agents set forth hereinbelow, are well known, or will be readily apparent in light of the instant disclosure, to one of ordinary skill in the art.

Especially preferred anti-obesity agents comprise those compounds selected from the group consisting of orlistat, sibutramine, bromocriptine, phentermine, ephedrine, leptin, phenylpropanolamine, and pseudoephedrine.

Representative anti-obesity agents for use in the combinations, pharmaceutical compositions, and methods of the invention can be prepared using methods known to one of ordinary skill in the art, for example, phentermine can be prepared as described in U.S. Pat. No. 2,408,345; sibutramine can be prepared as described in U.S. Pat. No. 4,929,629; bromocriptine can be prepared as described in U.S. Pat. Nos. 3,752,814 and 3,752,888; and orlistat can be prepared as described in U.S. Pat. Nos. 5,274,143; 5,420,305; 5,540, 917; and 5,643,874. All of the above recited U.S. patents are incorporated herein by reference.

The present invention further provides methods of treating $β_3$ adrenergic receptor-mediated diseases, conditions, or disorders in an animal in need of such treatment that comprise administering to the animal a therapeutically effective amount of: (1) a compound of the present invention; (2) a combination of a compound of the present invention with an anti-obesity agent; (3) a pharmaceutical composition comprising a therapeutically effective amount of a compound of the present invention and a pharmaceutically acceptable vehicle, carrier, diluent or mixture thereof; or (4) a pharmaceutical composition comprising a therapeutically effective amount of a compound of the present invention in combination with an anti-obesity agent and a pharmaceutically acceptable vehicle, carrier, or diluent or mixture thereof.

Preferably, the $\beta_3$ adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ucler, gastritis, hypercholesterolemia, cardiovascular disease, urinary incontinence, depression, prostate disease, dyslipidemia, and airway inflammatory disorder. Accordingly, the compounds of the present invention are useful in treating or preventing $\beta_3$ adrenergic receptor-mediated diseases, conditions, or disorders. Consequently, the compounds of the present invention (including the compositions and processes used therein) may be used in the manufacture of a medicament for the therapeutic applications described herein The invention further provides methods of increasing the lean meat content in an edible animal (i.e., food source animal) which comprises administering to the edible animal: (1) a lean meat increasing amount of a compound of the present invention; (2) a lean meat increasing amount of a compound of the present invention in combination with an anti-obesity agent; (3) a pharmaceutical composition comprising a lean meat increasing amount of a compound of the present invention and a pharmaceutically acceptable vehicle, carrier, diluent or mixture thereof; or (4) a pharmaceutical composition comprising a lean meat increasing amount of a compound of the present invention in combination with an anti-obesity agent and a pharmaceutically acceptable vehicle, carrier, diluent or mixture thereof.

The compounds of the present invention can be administered to a patient at dosage levels in the range of from about 0.01 to about 1,000 mg per day. However, some variability in the general dosage range may be required depending upon the age and weight of the subject being treated, the intended route of administration, the particular anti-obesity agent being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms, in light of this disclosure, will be well known to one of ordinary skill in the art.

The dosage of the anti-obesity agent will also be generally dependent upon a number of factors including the health of the subject being treated, the extent of treatment desired, the nature and kind of concurrent therapy, if any, and the frequency of treatment and the nature of the effect desired. In general, the dosage range of the anti-obesity agent is in the range of from about 0.001 to about 100 mg/kg body weight of the individual per day, preferably from about 0.01 to about 100 mg/kg body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and an anti-obesity agent is administered to a subject in need of such treatment, preferably in the form of a pharmaceutical composition. In the combination aspect of the invention, the compound of the present invention and the anti-obesity agent may be administered either separately or together (e.g., in a pharmaceutical composition comprising both). It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and an anti-obesity agent are administered together, such administration can be sequential in time or simultaneous with the simultaneous method being generally preferred. For sequential administration, a compound of the present invention and the anti-obesity agent can be administered in any order. It is generally preferred that such administration be oral. It is especially preferred that such administration be oral and simultaneous. When a compound of the present invention and the anti-obesity agent are administered sequentially, the administration of each can be by the same or by different methods.

According to the methods of the invention, a compound of the present invention or a combination of a compound of the present invention and an anti-obesity agent is preferably administered in the form of a pharmaceutical composition comprising a pharmaceutically acceptable carrier, vehicle, diluent or mixture thereof. Accordingly, a compound of the present invention or a combination of a compound of the present invention with an anti-obesity agent can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), buccal, or nasal dosage form.

Compositions suitable for parenteral injection may comprise pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the drug (e.g., a compound of the present invention) is admixed (homogeneously or heterogeneously) with at least one inert customary pharmaceutical excipient (or carrier) such as (a) sodium citrate or dicalcium phosphate; (b) fillers or extenders (e.g., starches, lactose, sucrose, mannitol, and silicic acid); (c) binders (e.g., carboxymethylcellulose, alginates, gelatin, polyvinylpyrrolidone, sucrose, and acacia); (d) humectants (e.g., glycerol); (e) disintegrating agents (e.g., agar-agar, calcium carbonate, potato or tapioca starch, alginic acid, certain complex silicates, and sodium carbonate); (f) solution retarders (e.g., paraffin); (g) absorption accelerators (e.g., quaternary ammonium compounds); (h) wetting agents (e.g., cetyl alcohol and glycerol monostearate); (i) adsorbents (e.g., kaolin and bentonite); and/or (j) lubricants (e.g., talc, calcium stearate, magnesium stearate, solid polyethylene glycols, and sodium lauryl sulfate). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the drug or compounds in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the drug, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and/or perfuming agents.

Suspensions, in addition to the drug, may further comprise suspending agents, e.g., ethoxylated isostearyl alcohols, polyoxyethylene sorbitol and sorbitan esters, microcrystalline cellulose, aluminum metahydroxide, bentonite, agar-agar, tragacanth, and the like, or mixtures of thereof.

Compositions for rectal or vaginal administration preferably comprise suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the compound.

Dosage forms for topical administration of the compounds of the present invention and combinations of the compounds of the present invention with anti-obesity agents may comprise ointments, powders, sprays and inhalants. The drugs are admixed under sterile condition with a pharmaceutically acceptable carrier, and any preservatives, buffers, or propellants that may be required. Opthalmic formulations, eye ointments, powders, and solutions are also intended to be included within the scope of the present invention.

Advantageously, the present invention also provides kits for use by a consumer having, or at risk of having, a disease or condition described herein, which can be ameliorated by $\beta_3$ agonists. Such kits include a suitable dosage form such as those described above and instructions describing the method of using such dosage form to mediate, reduce or prevent $\beta_3$ adrenergic receptor-mediated diseases, conditions, or disorders in an animal (in particular, a human). The instructions would direct the consumer or medical personnel to administer the dosage form according to administration modes known to those skilled in the art. Such kits could advantageously be packaged and sold in single or multiple kit units.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of the present invention and a second pharmaceutical agent (i.e., anti-obesity agent) as described above. The kit comprises a container (e.g., a divided bottle or a divided foil packet). Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

The following paragraphs describe exemplary formulations, dosages, etc. useful for non-human animals. The administration of the compounds of the present invention and combinations of the compounds of the present invention with anti-obesity agents can be effected orally or non-orally (e.g, by injection).

An amount of a compound of the present invention or combination of a compound of the present invention with an anti-obesity agent is administered such that an effective dose is received. Generally, a daily dose that is administered orally to an animal is between about 0.01 and about 1,000 mg, preferably between about 0.01 and about 300 mg. The exact amount will vary depending on the type of animal being treated.

Conveniently, the inventive compound can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, the inventive compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of drug per ton of feed, the optimum amount for these animals usually being about 50 to about 300 grams per ton of feed.

The preferred poultry and domestic pet feeds usually contain about 1 to about 400 grams and preferably about 10 to about 400 grams of the compound per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of a compound of the present invention to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound, pharmaceutical composition, or combination of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry and swine breeders, utilization of the method of the present invention yields leaner animals which command higher sale prices from the meat industry.

The embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials and reagents are generally available from commerical sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI)

were obtained on a Hewlett-Packard™ 5989 instrument (ammonia ionization, PBMS: available from Hewlett-Packard Company, Palo Alto, Calif.). Where the intensity of chlorine or bromine-containing ions is described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line ($\lambda$=589 nm) at the indicated temperature and are reported as follows $[\alpha]_D^{temp}$, concentration (c=g/100 mL), and solvent.

Column chromatography was performed with either Baker™ silica gel (40 $\mu$m; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

The following preparations describe the synthesis of intermediates used in Examples 1–3.

Preparations

Preparation of 1(R)-(3-Chloro-phenyl)-2-[1,1-dimethyl-2-(4-nitro-phenyl)-ethylamino]-ethanol (I-1a):

A solution of 2.2 g of 2-amino-2-methyl-1-(4-nitrophenyl)propane (prepared by the procedures described in J. Milecki, et al. *J. Med. Chem.*, 30, 1563 (1987)) and N-trimethylsilylacetamide (1.6 g) in 2.2 mL DMSO was stirred for 30 min, then (R)-3-chlorostyrene oxide (1.8 g) was added and the resulting solution was stirred at 95° C. for 22 h. The reaction solution was allowed to cool, poured over a mixture of ice (30 g) and 6 N aqueous hydrochloric acid (10 mL). A small portion of MeOH was added to produce a homogenous solution, which was stirred for 30 min. The resulting solution was basified with saturated aqueous sodium carbonate, extracted with ethyl acetate, the organic phase dried ($Na_2SO_4$) and concentrated in vacuo to afford 4.3 g of the title compound (I-1a) as an orange oil.

Preparation of 5(R)-(3-Chloro-phenyl)-3-[1,1-dimethyl-2-(4-nitro-phenyl)-ethyl]-oxazolidin-2-one (I-1b):

To a cooled (0° C.), stirred solution of 4.3 g of 1(R)-(3-chloro-phenyl)-2-[1,1-dimethyl-2-(4-nitro-phenyl)-ethylamino]-ethanol (I-1a) in 23 mL of dichloromethane was added 1,1-carbonyldiimidazole (2.1 g) and the resulting solution was allowed to slowly warm to ambient temperature, stirring a total of 22 h. The reaction solution was concentrated in vacuo and flash chromatographed on silica gel (20% ethyl acetate:hexanes) to afford 3.3 g of the title compound (I-1b) as a yellow oil.

Preparation of 3(R)-[2-(4-Amino-phenyl)-1,1-dimethyl-ethyl]-5-(3-chloro-phenyl)-oxazolidin-2-one (I-1c):

A solution of 1.8 g of 5(R)-(3-chloro-phenyl)-3-[1,1-dimethyl-2-(4-nitro-phenyl)-ethyl]-oxazolidin-2-one (I-1b) and stannous chloride (5.4 g) in 19 mL EtOH were heated at 70° C. for 2 h. The yellow solution was concentrated in vacuo, water added and the mixture was partitioned between ethyl acetate and saturated aqueous sodium bicarbonate. The aqueous phase was reextracted with ethyl acetate, the combined organic layers washed with brine, dried ($Na_2SO_4$) and concentrated in vacuo to afford 1.6 g of the title compound (1-1c) as an light-yellow foam.

Preparation of Piperidine-1-sulfonic acid (4-{2-[5(R)-(3-chloro-phenyl)-2-oxo-oxazolidin-3-yl]-2-methyl-propyl}-phenyl)-amide (I-1d):

To a cooled (0° C.), stirred solution of 235 mg of 3(R)-[2-(4-amino-phenyl)-1,1-dimethyl-ethyl]-5-(3-chloro-phenyl)-oxazolidin-2-one (I-1c) and triethylamine (0.4 mL) in 1,2-dichloroethane (0.5 mL) was added dropwise a solution of N-piperidinylsulfamoyl chloride (250 mg) in 1,2-dichloroethane (1 mL). After 15 min, the reaction was warmed to 65° C. and maintained at this temperature for 22 h. The reaction solution was diluted in ethyl acetate, washed with water, brine, dried ($Na_2SO_4$) and concentrated in vacuo. The resulting brown oil was chromatographed on a Biotage® F40M column (gradient of 20% to 40% ethyl acetate/hexanes) to afford 213 mg of the title compound (I-1d) as a colorless foam.

Preparation of 2-Chloro-5-formylpyridine (I-2a):

To a cooled (5° C.), stirred solution of 2-chloro-5-cyanopyridine (25.0 g) in anhydrous toluene (540 mL) was added a 1 M solution of diisobutylaluminum hydride (189 mL) over a 30-min period. The resulting red-colored solution was treated with methanol (50 mL) and 2M sulfuric acid (150 mL), sequentially. The resulting biphasic solution was allowed to warm to ambient temperature and stirred for 1 h. The reaction mixture was extracted with ethyl acetate, the combined organic layers were washed with saturated aqueous sodium bicarbonate and saturated aqueous brine. The organic phase was stirred over activated charcoal for 20 min, dried over anhydrous sodium sulfate and concentrated in vacuo to afford 23.5 g of the title compound (I-2a) as a light-yellow colored solid.

$^1H$ NMR ($CDCl_3$): $\delta$=10.08 (s, 1H); 8.85 (s, 1H); 8.12 (d, 1H); 7.50 (d, 1H).

Preparation of 2-Chloro-5-vinylpyridine (I-2b):

To a cooled (5° C.), stirred slurry of methyltriphenylphosphonium bromide (75.7 g) in tetrahydrofuran (530 mL) was added potassium t-butoxide (23.8 g) portionwise over a 5-min period to produce a yellow slurry. After 30 min, 2-chloro-5-formylpyridine (25.0 g) was added in one portion to produce a purple colored slurry. After an additional 30 min, the reaction mixture was treated with saturated aqueous ammonium chloride (200 mL) and a majority of the tetrahydrofuran was removed in vacuo. The resulting mixture was washed with ethyl acetate, the combined organic layers washed with saturated aqueous brine, stirred over activated charcoal for 20 min, dried over anhydrous sodium sulfate and concentrated in vacuo. The resulting semi-solid was stirred for 30 min with a solution of 2:1 diethyl ether/petroleum ether (375 mL), filtered and the solids washed with an additional portion of 2:1 diethyl ether/petroleum ether (300 mL). The combined filtrates were concentrated in vacuo, pre-loaded on 60 g of silica gel and chromatographed over 700 g of silica gel eluting with a gradient of ethyl acetate (0–8%)/hexanes to afford 15.2 g of the title compound (I-2b) as a colorless oil.

$^1H$ NMR ($CDCl_3$): $\delta$=8.35 (s, 1H); 7.69 (d, 1H); 7.27 (d, 1H); 6.65 (dd, 1H); 5.79 (d, 1H); 5.40 (d, 1H).

(R)-1-(6-Chloro-,pyridin-3-yl)-ethane-1,2-diol (I-2c):

To a cooled (5° C.), stirred slurry of AD-Mix-β® (150 g) in water (530 mL) and t-butanol (450 mL) was added a solution of 2-chloro-5-vinylpyridine (15.0 g) in t-butanol (80 mL). After 6 h, solid sodium sulfite (160 g) was added and the resulting slurry was allowed to stir at ambient temperature for 30 min. This mixture was extracted with ethyl acetate (3×), the combined organic layers were washed with saturated aqueous brine, dried over sodium sulfate and concentrated in vacuo. The resulting oil was chromatographed on 500 g of silica gel eluting with a gradient of ethyl acetate (70–80%)/hexanes to afford 17.8 g of the title compound (I-2c) as a colorless oil.

$^1H$ NMR ($CDCl_3$): $\delta$=8.35 (s, 1H); 7.71 (d, 1H); 7.30 (d, 1H); 4.85 (dd, 1H); 3.79 (d, 1H); 3.63 (dd, 1H).

(R)-Toluene-4-sulfonic acid 2-(6-chloro-pyridin-3-yl)-2-hydroxy-ethyl ester (I-2d):

To a cooled (50° C.), stirred solution of (R)-1-(6-chloro-pyridin-3-yl)-ethane-1,2-diol (17.8 g) in anhydrous pyridine (100 mL) was added p-toluenesulfonyl chloride (19.5 g) in one portion. After 20 min, the cooling bath was removed and stirring was continued an additional 2 h. The reaction solution was concentrated in vacuo, azeotroped with toluene (2×), diluted in ethyl acetate, washed with half-saturated aqueous brine, saturated aqueous brine, dried over sodium sulfate and concentrated in vacuo. The resulting solids were recrystallized from ethyl acetate/hexanes to afford 23.3 g of the title compound (I-2d) as colorless crystals.

$^1$H NMR (CDCl$_3$): δ=8.29 (s, 1H); 7.72 (d, 2H); 7.64 (d, 1H); 7.32 (d, 2H); 7.28 (d, 1H); 5.00 (dd, 1H); 4.09 (AB pattern, 2H); 2.44 (s, 3H).

(R)-Toluene-4-sulfonic acid 2-(tert-butyl-dimethyl-silanyloxy)-2-(6-chloro-pyridin-3-yl)-ethyl ester (I-2e):

To a cooled (50° C.), stirred solution of (R)-toluene-4-sulfonic acid 2-(6-chloro-pyridin-3-yl)-2-hydroxy-ethyl ester (4.9 g) and imidazole (2.0 g) in anhydrous dimethylformamide (14 mL) was added t-butyldimethylsilyl chloride (2.8 g). The reaction mixture was allowed to warm to room temperature and stirring was continued for 18 h. Ethyl acetate was added, followed by washing with water (2×), drying over sodium sulfate and concentration in vacuo to afford an oil. Chromatography (Flash 40M®) utilizing 10% ethyl acetate/hexanes afforded 5.6 g of the title compound (I-2e) as a colorless oil.

$^1$H NMR (CDCl$_3$): δ=8.24 (s, 1H); 7.64 (d, 2H); 7.56 (d, 1H); 7.28 (d, 2H); 7.23 (d, 1H); 4.88 (dd, 1H); 3.95 (AB pattern, 2H); 2.44 (s, 3H); 0.83 (s, 6H); 0.06 (s, 3H); −0.07 (s, 3H).

[2(R)-(tert-Butyl-dimethyl-silanyloxy)-2-(6-chloro-pyridin-3-yl)-ethyl]-[1,1-dimethyl-2-(4-nitro-phenyl)-ethyl]-amine (I-2f):

A solution of (R)-toluene-4-sulfonic acid 2-(tert-butyl-dimethyl-silanyloxy)-2-(6-chloro-pyridin-3-yl)-ethyl ester (12.0 g) and 11.4 g of 2-amino-2-methyl-1-(4-nitrophenyl)propane (prepared by the method described in J. Milecki, et al. *J. Med. Chem.*, 30, 1563 (1987)) in DMSO (30 mL) was stirred at 100° C. for 48 h. The reaction solution was partitioned between ethyl ether/water, the resulting organic layer washed with water (3×), brine, dried over sodium sulfate and concentrated in vacuo to afford an oil. Flash chromatography on silica gel (20% to 50% ethyl acetate/hexanes) afforded 8.0 g of the title compound (I-2f) as a golden oil.

4-{2(R)-[2-(tert-Butyl-dimethyl-silanyloxy)-2-pyridin-3-yl-ethylamino]-2-methyl-propyl}-phenylamine (I-2g):

To a slurry of [2(R)-(tert-butyl-dimethyl-silanyloxy)-2-(6-chloro-pyridin-3-yl)-ethyl]-[1,1-dimethyl-2-(4-nitrophenyl)-ethyl]-amine (8.0 g) and 10% palladium-on-carbon (4.0 g) in MeOH (200 mL) was added ammonium formate (22 g) and the resulting mixture was stirred at ambient temperature for 3 h. The reaction mixture was filtered through Celite®, washing with MeOH and the filtrate concentrated in vacuo. The resulting semi-solid was partitioned between ethyl acetate and half-saturated aqueous sodium bicarbonate, the organic phase was separated, dried (Na$_2$SO$_4$) and concentrated in vacuo to afford 6.5 g of the title compound (I-2g) as a dark oil.

Preparation of 2-[2-(tert-Butyl-dimethyl-silanyloxy)-2-(6-chloro-pyridin-3-yl)-ethylamino]-ethanol (I-3a):

A solution of ethanolamine (1.2 mL), (R)-toluene-4-sulfonic acid 2-(tert-butyl-dimethyl-silanyloxy)-2-(6-chloro-pyridin-3-yl)-ethyl ester (2.2 g) and diisopropylethylamine (1.3 mL) in DMSO (5 mL) was heated at 80° C. for 4 h. After cooling, the reaction solution was diluted into ethyl acetate, washed with water (2×), brine, dried (Na$_2$SO$_4$) and concentrated in vacuo to afford the title compound (I-3a) as an oil.

Preparation of [2-(tert-Butyl-dimethyl-silanyloxy)-2-(6-chloro-pyridin-3-yl)-ethyl]-(2-hydroxy-ethyl)-carbamic acid tert-butyl ester (I-3b):

To a stirred solution of 2-[2-(tert-butyl-dimethyl-silanyloxy)-2-(6-chloro-pyridin-3-yl)-ethylamino]-ethanol (1.6 g) in THF (15 mL) was added di-tert-butyl dicarbonate (1.6 g). After 1.5 h, the reaction solution was concentrated in vacuo and chromatographed on a Biotage® F40M column (gradient of 10% to 20% ethyl acetate/hexanes) to afford 1.8 g of the title compound (I-1b) as an oil.

Preparation of [2-(tert-Butyl-dimethyl-silanyloxy)-2-(6-chloro-pyridin-3-yl)-ethyl]-[2-(4-nitro-phenoxy)-ethyl]-carbamic acid tert-butyl ester (I-3c):

To a cooled (0° C.), stirred solution of triphenylphosphine (629 mg) in THF (6 mL) was added diisopropylazodicarboxylate (0.5 mL) dropwise and the resulting thick white slurry was stirred for 45 min. A solution of [2-(tert-butyl-dimethyl-silanyloxy)-2-(6-chloro-pyridin-3-yl)-ethyl]-(2-hydroxy-ethyl)-carbamic acid tert-butyl ester (515 mg) and 4-nitrophenol (332 mg) in THF (5 mL) was added dropwise to produce a yellow slurry. After an additional 1 h period, the cooling bath was removed and the mixture was allowed to stir at ambient temperature for 20 h. This mixture was concentrated in vacuo and chromatographed on a Biotage® F40M column (gradient of 10% to 15% ethyl acetate/hexanes) to afford 530 mg of the title compound (I-3c) as a colorless foam.

Preparation of [2-(4-Amino-phenoxy)-ethyl]-[2-(tert-butyl-dimethyl-silanyloxy)-2-pyridin-3-yl-ethyl]-carbamic acid tert-butyl ester (I-3d):

To a stirred slurry of [2-(tert-butyl-dimethyl-silanyloxy)-2-(6-chloro-pyridin-3-yl)-ethyl]-[2-(4-nitro-phenoxy)-ethyl]-carbamic acid tert-butyl ester (530 mg) and 10% palladium-on-carbon (530 mg) in MeOH (20 mL) was added ammonium formate (1.2 g). After 1.5 h, the reaction mixture was filtered through Celite® washing with methanol and concentrated in vacuo. The residue was suspended in half-saturated aqueous sodium bicarbonate, washed with ethyl acetate (3×), the combined organic phases were dried (Na$_2$SO$_4$) and concentrated in vacuo. The resulting oil was chromatographed on a Biotage® F40S column (40% ethyl acetate/hexanes) to afford 290 mg of the title compound (I-3d) as a colorless oil.

Preparation of [2-(4-N-(Dimethylsulfamoyl)amino-phenoxy)-ethyl]-[2-(tert-butyl-dimethyl-silanyloxy)-2-pyridin-3-yl-ethyl]-carbamic acid tert-butyl ester (I-3e):

To a cooled (−35° C.), stirred solution of [2-(4-amino-phenoxy)-ethyl]-[2-(tert-butyl-dimethyl-silanyloxy)-2-pyridin-3-yl-ethyl]-carbamic acid tert-butyl ester (143 mg) and pyridine (69 mg) in 1,2-dichloroethane (1 mL) was added a solution of dimethylsulfamoyl chloride (63 mg) in 1,2-dichloroethane (0.3 mL) dropwise. The resulting solution was allowed to warm to ambient temperature and was stirred for 22 h and then heated at 60° C. for an additional 6 h. After cooling, the resulting red solution was diluted into ethyl acetate, washed with half-saturated aqueous ammonium chloride, dried (Na$_2$SO$_4$) and concentrated in vacuo. The resulting oil was chromatographed on a Biotage® F25M column (50% ethyl acetate/hexanes) to afford 160 mg of the title compound (I-3e) as a colorless oil.

Example 1

N-[4-[2-[[(2R)-2-(3-Chlorophenyl)-2-hydroxyethyl]amino]-2-methylpropyl]phenyl]-1-piperidinesulfonamide, dihydrochloride (1A):

A solution of 210 mg of piperidine-1-sulfonic acid (4-{2-[5(R)-(3-chloro-phenyl)-2-oxo-oxazolidin-3-yl]-2-methylpropyl}-phenyl)-amide (I-1d) and powdered potassium hydroxide (772 mg) in EtOH (5 mL)/DMSO (1 mL) was stirred at 80° C. for 47 h. The reaction solution was cooled and treated with 3 N aqueous hydrochloric acid (8 mL). The resulting mixture was diluted into ethyl acetate, washed with saturated aqueous sodium carbonate, brine, dried ($Na_2SO_4$) and concentrated in vacuo. The resulting brown oil was chromatographed on a Biotage® F12M column (5% MeOH:dichloromethane) to afford 143 mg of the title compound (1) as a golden oil.

To a solution of the above oil in ethyl acetate (3 mL) was added a solution of 1 N hydrochloric acid in ethyl ether (1 mL), the resulting solution was stirred for 30 min and then concentrated in vacuo to afford a foam. This foam was scratched in the presence of diethyl ether to afford 147 mg of the title compound (1A) as an off-white solid after filtering and drying in vacuo; ms (Cl) m/z=466.1 (M+1). $^1$H NMR ($CDCl_3$) was consistent with compound (1A).

[4-[2-[[(2R)-2-(3-Chlorophenyl)-2-hydroxyethyl]amino]ethyl]phenyl]trimethyl-sulfamide, dihydrochloride (1B):

To a cooled (0° C.) solution 255 mg of dimethylamino-1-sulfonic acid (4-{2-[5(R)-(3-chloro-phenyl)-2-oxo-oxazolidin-3-yl]-2-ethyl}-phenyl)-amide in DMF (1.2 mL) was added lithium bis(trimethylsilyl)amide (1 M in THF, 0.9 mL) dropwise and the resulting yellow solution was stirred for 30 min. Methyl iodide (0.08 mL) was added and after 1.5 h the reaction solution was poured into saturated aqueous ammonium chloride. The resulting mixture was extracted with ethyl acetate, dried ($Na_2SO_4$) and concentrated in vacuo to afford 280 mg of a yellow oil.

This oil was treated with potassium hydroxide in EtOH, purified and hydrochloride salt prepared as described above to afford 127 mg of the title compound (1B) as a white solid; ms (Cl) m/z=412.2 (M+1). $^1$H NMR ($CDCl_3$) was consistent with compound (1 B).

The following compounds were prepared using procedures analogous to those described above:

N'-[4-[2-[[(2R)-2-(3-Chlorophenyl)-2-hydroxyethyl]amino]ethyl]phenyl]-N, N-dimethyl-sulfamide, dihydrochloride) (1C):

ms (Cl) m/z=398.1 (M+1). $^1$H NMR ($CDCl_3$) was consistent with compound (1C).

N-[4-[2-[[(2R)-2-(3-Chlorophenyl)-2-hydroxyethyl]amino]ethyl]phenyl]-1-piperidinesulfonamide (1D):

ms (Cl) m/z=438.2 (M+1). $^1$H NMR ($CDCl_3$) was consistent with compound (1D).

N-[4-[2-[[(2R)-2-(3-Chlorophenyl)-2-hydroxyethyl]amino]ethyl]phenyl]-N'-cyclohexyl-sulfamide (1E):

ms (Cl) m/z=452.3 (M+1). $^1$H NMR ($CDCl_3$) was consistent with compound (1E).

N-[4-[2-[[(2R)-2-(3-Chlorophenyl)-2-hydroxyethyl]amino]ethyl]phenyl]-1-piperidinesulfonamide, dihydrochloride (1F):

ms (Cl) m/z=365.1 (M+1). $^1$H NMR ($CDCl_3$) was consistent with compound (1F).

N'-[4-[2-[[(2R)-2-(3-Chlorophenyl)-2-hydroxyethyl]amino]ethyl]phenyl]-N-cyclohexyl-N-methyl-sulfamide, dihydrochloride (1G):

ms (Cl) m/z=466.3 (M+1). $^1$H NMR ($CDCl_3$) was consistent with compound (1G).

Example 2

N-(Cyclopropylmethyl)-N'-[4-[2-[[(2(R)-[2-(tert-butyl-dimethyl-silanyloxy)-2-(3-piridinyl)ethyl]amino]-2-methylpropyl]phenyl]-sulfamide (2A):

To a cooled (−40° C.), stirred solution of 150 mg of 4-{2(R)-[2-(tert-butyl-dimethyl-silanyloxy)-2-pyridin-3-yl-ethylamino]-2-methyl-propyl}-phenylamine (I-2g) and pyridine (0.14 mL) in 1,2-dichloroethane (0.25 mL) was added a solution of N-(cyclopropylmethyl)sulfamoyl chloride (96 mg) in 1,2-dichloroethane (0.25 mL). The resulting solution was stirred for 30 min at −40° C., then allowed to warm to ambient temperature and stir an additional 1 h. The reaction solution was diluted into ethyl acetate, washed with half-saturated aqueous sodium bicarbonate, brine, dried ($Na_2SO_4$) and concentrated in vacuo. The resulting oil was flash chromatographed on silica gel (gradient of 0% to 4% MeOH:dichloromethane) to afford 155 mg of the title compound (2A) as a foam. $^1$H NMR ($CDCl_3$) was consistent with compound (2A).

N-(Cyclopropylmethyl)-N'-[4-[2-[[(2R)-2-hydroxy-2-(3-pyridinyl)ethyl]amino]-2-methylpropyl]phenyl]-sulfamide (2B):

To a stirred solution of 155 mg of N-(cyclopropylmethyl)-N'-[4-[2-[[(2(R)-[2-(tert-butyl-dimethyl-silanyloxy)-2-(3-pyridinyl)ethyl]amino]-2-methylpropyl]phenyl]-sulfamide (2A) in THF (2 mL) was added a 1 M solution of tetrabutylammonium fluoride in THF (0.44 mL). After stirring for 18 h, the reaction solution was concentrated in vacuo, diluted into ethyl acetate, washed with saturated ammonium chloride, brine, dried ($Na_2SO_4$) and concentrated in vacuo. Flash chromatography on silica gel (gradient of 10% to 14% MeOH:dichloromethane) afforded 71 mg of the title compound (2B). $^1$H NMR ($CDCl_3$) was consistent with compound (2B).

N-(Cyclopropylmethyl)-N'-[4-[2-[[(2R)-2-hydroxy-2-(3-pyridinyl)ethyl]amino]-2-methylpropyl]phenyl]-sulfamide, dihydrochloride (2C):

To a stirred solution of 71 mg of N-(cyclopropylmethyl)-N'-[4-[2-[[(2R)-2-hydroxy-2-(3-pyridinyl)ethyl]amino]-2-methylpropyl]phenyl]-sulfamide (2B) in MeOH (1.5 mL) was added 4 N hydrochloric acid in p-dioxane (0.42 mL). After 10 minutes, the reaction solution was concentrated in vacuo to afford 75 mg of the title compound (2C) as a white solid; ms (Cl) m/z=419.4 (M+1). $^1$H NMR ($CDCl_3$) was consistent with compound (2C).

The following compounds were prepared employing procedures analogous to those described above with the appropriate starting materials:

N-(1,1-Dimethyl-2-phenylethyl)-N'-[4-[2-[[(2R)-2-hydroxy-2-(3-pyridinyl)ethyl]amino]-2-methylpropyl]phenyl]-sulfamide, dihydrochloride (2D):

ms (Cl) m/z=497.3 (M+1). $^1$H NMR ($CDCl_3$) was consistent with compound (2D).

N-[4-[2-[[(2R)-2-Hydroxy-2-(3-pyridinyl)ethyl]amino]-2-methylpropyl]phenyl]-2,6-dimethyl-, (2R, 6S)-4-morpholinesulfonamide, dihydrochloride (2E):

ms=(Cl) m/z 463.4 (M+1). $^1$H NMR ($CDCl_3$) was consistent with compound (2E).

N-[4-[2-[[(2R)-2-Hydroxy-2-(3-pyridinyl)ethyl]amino]-2-methylpropyl]phenyl]-4-methyl-1-piperidinesulfonamide, dihydrochloride (2F):

ms (Cl) m/z=447.2 (M+1). $^1$H NMR (CDCl$_3$) was consistent with compound (2F).

N-[4-[2-[[(2R)-2-Hydroxy-2-(3-pyridinyl)ethyl]amino]-2-methylpropyl]phenyl]-3,5-dimethyl-, (3R,5S)-1-piperidinesulfonamide, dihydrochloride (2G):

ms (Cl) m/z=461.4 (M+1). $^1$H NMR (CDCl$_3$) was consistent with compound (2G).

N-[4-[2-[[(2R)-2-Hydroxy-2-(3-pyridinyl)ethyl]amino]-2-methylpropyl]phenyl]-4-phenyl-1-piperidinesulfonamide, dihydrochloride (2H):

ms (Cl) m/z=509.4 (M+1). $^1$H NMR (CDCl$_3$) was consistent with compound (2H).

N-[4-[2-[[(2R)-2-Hydroxy-2-(3-pyridinyl)ethyl]amino]-2-methylpropyl]phenyl]-N'-[(1S)-1-phenylethyl]-sulfamide, dihydrochloride (2I):

ms (Cl) m/z=469.4 (M+1). $^1$H NMR (CDCl$_3$) was consistent with compound (2I).

N-Cyclohexyl-N'-[4-[2-[[(2R)-2-hydroxy-2-(3-pyridinyl)ethyl]amino]-2-methylpropyl]phenyl]-sulfamide, dihydrochloride (2J):

ms (Cl) m/z=447.3 (M+1). $^1$H NMR (CDCl$_3$) was consistent with compound (2J).

N-[4-[2-[[(2R)-2-Hydroxy-2-(3-pyridinyl)ethyl]amino]-2-methylpropyl]phenyl]-octahydro-(4aR,8aR)-2(1H)-isoquinolinesulfonamide, dihydrochloride (2K):

ms (Cl) m/z=487.4 (M+1). $^1$H NMR (CDCl$_3$) was consistent with compound (2K).

N-[4-[2-[[(2R)-2-Hydroxy-2-(3-pyridinyl)ethyl]amino]-2-methylpropyl]phenyl]-N'-phenyl-sulfamide, dihydrochloride (2L):

ms (Cl) m/z=441.3 (M+1). $^1$H NMR (CDCl$_3$) was consistent with compound (2L).

N'-[4-[2-[[(2R)-2-Hydroxy-2-(3-pyridinyl)ethyl]amino]-2-methylpropyl]phenyl]-N,N-dimethyl-sulfamide, dihydrochloride (2M):

ms (Cl) m/z=393.3 (M+1). $^1$H NMR (CDCl$_3$) was consistent with compound (2M).

N-(Cyclohexylmethyl)-N'-[4-[2-[[(2R)-2-hydroxy-2-(3-pyridinyl)ethyl]amino]-2-methylpropyl]phenyl]-sulfamide, dihydrochloride (2N):

ms (Cl) m/z=461.4 (M+1). $^1$H NMR (CDCl$_3$) was consistent with compound (2N).

N-Cyclopropyl-N'-[4-[2-[[(2R)-2-hydroxy-2-(3-pyridinyl)ethyl]amino]-2-methylpropyl]phenyl]-sulfamide, dihydrochloride (2O):

ms (Cl) m/z=405.3 (M+1). $^1$H NMR (CDCl$_3$) was consistent with compound (2O).

N-[4-[2-[[(2R)-2-Hydroxy-2-(3-pyridinyl)ethyl]amino]-2-methylpropyl]phenyl]-3-methyl-3-phenyl-1-piperidinesulfonamide, dihydrochloride (2P):

ms (Cl) m/z=523.4 (M+1). $^1$H NMR (CDCl$_3$) was consistent with compound (2P).

N-[4-[2-[[(2R)-2-Hydroxy-2-(3-pyridinyl)ethyl]amino]-2-methylpropyl]phenyl]-3,3-dimethyl-1-piperidinesulfonamide, dihydrochloride (2Q):

ms (Cl) m/z=461.3 (M+1). $^1$H NMR (CDCl$_3$) was consistent with compound (2Q).

N-[4-[2-[[(2R)-2-Hydroxy-2-(3-pyridinyl)ethyl]amino]-2-methylpropyl]phenyl]-2,3-dihydro-spiro[1H-indene-1,3'-piperidine]-1'-sulfonamide dihydrochloride (2R):

ms (Cl) m/z=535.4 (M+1). $^1$H NMR (CDCl$_3$) was consistent with compound (2R).

N-(Cyclopropylmethyl)-N'-[4-[2-[[(2R)-2-hydroxy-2-(3-pyridinyl)ethyl]amino]-2-methylpropyl]phenyl]-sulfamide, dihydrochloride (2S):

ms (Cl) m/z=419.4 (M+1). $^1$H NMR (CDCl$_3$) was consistent with compound (2S).

N-[4-[2-[[(2R)-2-Hydroxy-2-(3-pyridinyl)ethyl]amino]-2-methylpropyl]phenyl]-N'-[(1R, 2S)-2-phenylcyclopropyl]-sulfamide, dihydrochloride (2T):

ms (Cl) m/z=481.3 (M+1). $^1$H NMR (CDCl$_3$) was consistent with compound (2T).

N-(2,3-Dihydro-1H-inden-1-yl)-N'-[4-[2-[[(2R)-2-hydroxy-2-(3-pyridinyl)ethyl]amino]-2-methylpropyl]phenyl]-sulfamide, dihydrochloride (2U):

ms (Cl) m/z=481.4 (M+1). $^1$H NMR (CDCl$_3$) was consistent with compound (2U).

N-(1R,2S,4S)-Endo-bicyclo[2.2.1]hept-2-yl-N'-[4-[2-[[(2R)-2-hydroxy-2-(3-pyridinyl)ethyl]amino]-2-methylpropyl]phenyl]-sulfamide, dihydrochloride (2V):

ms (Cl) m/z=459.5 (M+1). $^1$H NMR (CDCl$_3$) was consistent with compound (2V).

N-[4-[2-[[(2R)-2-Hydroxy-2-(3-pyridinyl)ethyl]amino]-2-methylpropyl]phenyl]-N'(2-methoxyethyl)-sulfamide, dihydrochloride (2W):

ms (Cl) m/z=423.4 (M+1). $^1$H NMR (CDCl$_3$) was consistent with compound (2W).

N-[4-[2-[[(2R)-2-Hydroxy-2-(3-pyridinyl)ethyl]amino]-2-methylpropyl]phenyl]-N'-[[(2S)-tetrahydro-2-furanyl]methyl]-sulfamide, dihydrochloride (2X):

ms (Cl) m/z=449.4 (M+1). $^1$H NMR (CDCl$_3$) was consistent with compound (2X).

N-[4-[2-[[(2R)-2-Hydroxy-2-(3-pyridinyl)ethyl]amino]-2-methylpropyl]phenyl]-4-methyl-1-piperazinesulfonamide, trihydrochloride (2Y):

ms (Cl) m/z=448.4 (M+1). $^1$H NMR (CDCl$_3$) was consistent with compound (2Y).

N-[4-[2-[[(2R)-2-Hydroxy-2-(3-pyridinyl)ethyl]amino]-2-methylpropyl]phenyl]-4-(phenylmethyl)-1-piperazinesulfonamide, dihydrochloride (2Z):

ms (Cl) m/z=524.5 (M+1). $^1$H NMR (CDCl$_3$) was consistent with compound (2Z).

N-Cyclobutyl-N'-[4-[2-[[(2R)-2-hydroxy-2-(3-pyridinyl)ethyl]amino]-2-methylpropyl]phenyl]-sulfamide, dihydrochloride (2AA):

ms (Cl) m/z=419.4 (M+1). $^1$H NMR (CDCl$_3$) was consistent with compound (2AA).

N-[4-[2-[[(2R)-2-Hydroxy-2-(3-pyridinyl)ethyl]amino]-2-methylpropyl]phenyl]-1-piperazinesulfonamide, trihydrochloride (2BB):

ms (Cl) m/z=434.4 (M+1). $^1$H NMR (CDCl$_3$) was consistent with compound (2BB).

N-[4-[2-[[(2R)-2-Hydroxy-2-(3-pyridinyl)ethyl]amino]-2-methylpropyl]phenyl]-N'-[1-(phenylmethyl)-4-piperidinyl]-sulfamide, trihydrochloride (2CC):

ms (Cl) m/z=538.5 (M+1). $^1$H NMR (CDCl$_3$) was consistent with compound (2CC).

N-[4-[2-[[(2R)-2-Hydroxy-2-(3-pyridinyl)ethyl]amino]-2-methylpropyl]phenyl]-N'-[(3S)-1-(phenylmethyl)-3-pyrrolidinyl]-sulfamide, trihydrochloride (2DD):

ms (Cl) m/z=524.1 (M+1). $^1$H NMR (CDCl$_3$) was consistent with compound (2DD).

N-[4-[2-[[(2R)-2-Hydroxy-2-(3-pyridinyl)ethyl]amino]-2-methylpropyl]phenyl]-N'-[(1S,2S)-2-(phenylmethoxy)cyclopentyl]-sulfamide, dihydrochloride (2EE):

ms (Cl) m/z=467.0 (M+1). $^1$H NMR (CDCl$_3$) was consistent with compound (2EE).

N'-[4-[2-[[(2R)-2-Hydroxy-2-(3-pyridinyl)ethyl]amino]ethyl]phenyl]-N,N-dimethyl-sulfamide, dihydrochloride (2FF):

ms (Cl) m/z=365.1 (M+1). $^1$H NMR (CDCl$_3$) was consistent with compound (2FF).

N-[4-[2-[[(2R)-2-Hydroxy-2-(3-pyridinyl)ethyl]amino]ethyl]phenyl]-1-piperidinesulfonamide, dihydrochloride (2GG):

ms (Cl) m/z=405.3 (M+1). $^1$H NMR (CDCl$_3$) was consistent with compound (2GG).

N-Cyclohexyl-N'-[4-[2-[[(2R)-2-hydroxy-2-(3-pyridinyl)ethyl]amino]ethyl]phenyl]-N-methyl-sulfamide, dihydrochloride (2HH):

ms (Cl) m/z=433.3 (M+1). $^1$H NMR (CDCl$_3$) was consistent with compound (2HH).

N-[4-[2-[[(2R)-2-Hydroxy-2-(3-pyridinyl)ethyl]amino]ethyl]phenyl]-4-(phenylmethyl)-1-piperidinesulfonamide, dihydrochloride (2II):

ms (Cl) m/z=495.4 (M+1). $^1$H NMR (CDCl$_3$) was consistent with compound (2II).

N-[4-[2-[[(2R)-2-Hydroxy-2-(3-pyridinyl)ethyl]amino]ethyl]phenyl]-4-methyl-1-piperidinesulfonamide, dihydrochloride (2JJ):

ms (Cl) m/z=419.3 (M+1). $^1$H NMR (CDCl$_3$) was consistent with compound (2JJ).

N-[4-[2-[[(2R)-2-Hydroxy-2-(3-pyridinyl)ethyl]amino]ethyl]phenyl]-hexahydro-1H-azepine-1-sulfonamide, dihydrochloride (2KK):

ms (Cl) m/z=419.3 (M+1). $^1$H NMR (CDCl$_3$) was consistent with compound (2KK).

N-[4-[2-[[(2R)-2-Hydroxy-2-(3-Pyridinyl)ethyl]amino]phenyl]-2,6-dimethyl-, (2R,6S)-4-morpholinesulfonamide, dihydrochloride (2LL):

ms (Cl) m/z=435.2 (M+1). $^1$H NMR (CDCl$_3$) was consistent with compound (2LL).

N'-[4-[2-[[(2R)-2-Hydroxy-2-(3-pyridinyl)ethyl]amino]ethyl]phenyl]-N-methyl-N-(2-phenylethyl)-sulfamide, dihydrochloride (2MM):

ms (Cl) m/z=455.1 (M+1). $^1$H NMR (CDCl$_3$) was consistent with compound (2MM).

N'-[4-[2-[[(2R)-2-Hydroxy-2-(3-pyridinyl)ethyl]amino]ethyl]phenyl]-N-methyl-N-(1-methylethyl)-sulfamide, dihydrochloride (2NN):

ms (Cl) m/z=393.3 (M+1). $^1$H NMR (CDCl$_3$) was consistent with compound (2NN).

N-[4-[2-[[(2R)-2-Hydroxy-2-(3-pyridinyl)ethyl]amino]ethyl]phenyl]-3,4-dihydro-2(1H)-isoquinolinesulfonamide, dihydrochloride (2OO):

ms (Cl) m/z=453.1 (M+1). $^1$H NMR (CDCl$_3$) was consistent with compound (2OO).

N-[4-[2-[[(2R)-2-Hydroxy-2-(3-pyridinyl)ethyl]amino]ethyl]phenyl]-2-(methoxymethyl)-, (2S)-1-pyrrolidinesulfonamide, dihydrochloride (2PP):

ms (Cl) m/z=435.1 (M+1). $^1$H NMR (CDCl$_3$) was consistent with compound (2PP).

N-[4-[2-[[(2R)-2-Hydroxy-2-(3-pyridinyl)ethyl]amino]ethyl]phenyl]-3,5-dimethyl-, (3R,5S)-1piperidinesulfonamide, dihydrochloride (2QQ):

ms (Cl) m/z=433.3 (M+1). $^1$H NMR (CDCl$_3$) was consistent with compound (2QQ).

N-(2, 3-Dihydro-1H-inden-2-yl)-N'-[4-[2-[[(2R)-2-hydroxy-2-(3-pyridinyl)ethyl]amino]ethyl]phenyl]-sulfamide, dihydrochloride (2RR):

ms (Cl) m/z=453.3 (M+1). $^1$H NMR (CDCl$_3$) was consistent with compound (2RR).

N-[4-[2-[[(2R)-2-Hydroxy-2-(3-pyridinyl)ethyl]amino]ethyl]phenyl]-4-phenyl-1-piperidinesulfonamide, dihydrochloride (2SS):

ms (Cl) m/z=481.4 (M+1). $^1$H NMR (CDCl$_3$) was consistent with compound (2SS).

N'-[4-[2-[[(2R)-2-Hydroxy-2-(3-pyridinyl)ethyl]amino]ethyl]phenyl]-N-methyl-N-phenyl-sulfamide, dihydrochloride (2TT):

ms (Cl) m/z=427.1 (M+1). $^1$H NMR (CDCl$_3$) was consistent with compound (2TT).

4-(1,1-Dimethylethyl)-N-[4-[2-[[(2R)-2-hydroxy-2-(3-pyridinyl)ethyl]amino]ethyl]phenyl]-1-piperidinesulfonamide, dihydrochloride (2UU):

ms (Cl) m/z=460.9 (M+1). $^1$H NMR (CDCl$_3$) was consistent with compound (2UU).

N-[4-[2-[[(2R)-2-Hydroxy-2-(3-pyridin yl)ethyl]
amino]ethyl]phenyl]-octahydro-(4aS,8aS)-2(1H)-
isoquinolinesulfonamide, dihydrochloride (2VV):

ms (Cl) m/z 459.1 (M+1). $^1$H NMR (CDCl$_3$) was consistent with compound (2VV).

N-Cyclohexyl-N'-[4-[2-[[(2R)-2-hydroxy-2-(3-
pyridinyl)ethyl]amino]ethyl]phenyl]-sulfamide,
dihydrochloride (2WW):

ms (Cl) m/z=419.1 (M+1). $^1$H NMR (CDCl$_3$) was consistent with compound (2WW).

3-Cyclohexyl-N-[4-[2-[[(2R)-2-hydroxy-2-(3-
pyridinyl)ethyl]amino]ethyl]phenyl]-1-
piperidinesulfonamide, dihydrochloride (2YY):

ms (Cl) m/z=487.4 (M+1). $^1$H NMR (CDCl$_3$) was consistent with compound (2YY).

4-Cyano-N-[4-[2-[[(2R)-2-hydroxy-2-(3-pyridinyl)
ethyl]amino]ethyl]phenyl]-4-phenyl-1-
piperidinesulfonamide, dihydrochloride (2ZZ):

ms (Cl) m/z=506.3 (M+1). $^1$H NMR (CDCl$_3$) was consistent with compound (2ZZ).

N-[4-[2-[[(2R)-2-Hydroxy-2-(3-pyridinyl)ethyl]
amino]ethyl]phenyl]-3-4-methoxyphenyl)methyl]-1-
pyrrolidinesulfonamide, dihydrochloride (2BA):

ms (Cl) m/z=511.1 (M+1). $^1$H NMR (CDCl$_3$) was consistent with compound (2BA).

N-[(1R,2S,4S)-Endo-bicyclo[2.2.1]hept-2-ylmethyl]-
N'-[4-[2-[[(2R)-2-hydroxy-2-(3-pyridinyl)ethyl]
amino]-2-methylpropyl]phenyl]-sulfamide,
dihydrochloride (2BC):

ms (Cl) m/z=445.1 (M+1). $^1$H NMR (CDCl$_3$) was consistent with compound (2BC).

N-[4-[2-[[(2R)-2-Hydroxy-2-(3-pyridinyl)ethyl]
amino]ethyl]phenyl]-5-methoxy-3,4-dihydro-spiro
[naphthalene-1(2H),4'-piperidine]-1'-sulfonamide,
dihydrochloride (2BD):

ms (Cl) m/z=551.5 (M+1). $^1$H NMR (CDCl$_3$) was consistent with compound (2BD).

N-[4-[2-[[(2R)-2-Hydroxy-2-(3-pyridinyl)ethyl]
amino]ethyl]phenyl]-1-(4-methylphenyl)-3-
azabicyclo[3.1.0]hexane-3-sulfonamide,
dihydrochloride (2BE):

ms (Cl) m/z=493.4 (M+1). $^1$H NMR (CDCl$_3$) was consistent with compound (2BE).

N-[4-[2-[[(2R)-2-hydroxy-2-(3-pyridinyl)ethyl]
amino]ethyl]phenyl]-7-(trifluoromethyl) -1,2,4,5-
tetrahydro-1,5-methano-3H-3-benzazepine-3-
sulfonamide, dihydrochloride (2BF):

ms (Cl) m/z=547.4 (M+1). $^1$H NMR (CDCl$_3$) was consistent with compound (2BF).

Example 3

N'-[4-[2-[[(2R)-2-Hydroxy-2-(3-pyridinyl)ethyl]
amino]ethoxy]phenyl]-N,N-dimethyl-sulfamide,
dihydrochloride (3A):

To a stirred solution of 159 mg of [2-(4-N-(dimethylsulfamoyl)amino-phenoxy)-ethyl]-[2-(tert-butyl-dimethyl-silanyloxy)-2-pyridin-3-yl-ethyl]-carbamic acid tert-butyl ester (I-3e) in THF (2 mL) was added 1 M tetra-n-butylammonium fluoride in THF (0.4 mL). After 16 h, the reaction solution was diluted into ethyl acetate, washed with saturated aqueous ammonium chloride, dried (Na$_2$SO$_4$) and concentrated in vacuo. The resulting oil was chromatographed on a Biotage® F25M column (50% ethyl acetate/hexanes) to afford a colorless oil (129 mg).

A solution of the above oil in MeOH (1.3 mL) and 4 N hydrochloric acid in p-dioxane (1 mL) was stirred for 2.5 h and concentrated in vacuo. The resulting gummy solid was treated with diethyl ether with scratching to afford 105 mg of the title compound (3A) as a white solid:

ms (Cl) m/z=379.2 (M-1). $^1$H NMR (CDCl$_3$) was consistent with compound (3A).

The following compound were prepared employing procedures analogous to those described above for the preparation of Compound 3A:

N-[4-[2-[[(2R)-2-Hydroxy-2-(3-pyridinyl)ethyl]
amino]ethoxy]phenyl]-4-methyl-1-
piperidinesulfonamide, dihydrochloride (3B):

ms (Cl) m/z=433.2(M-1). $^1$H NMR (CDCl$_3$) was consistent with compound (3B).

BIOLOGICAL ASSAYS

The utility of the compounds of the present invention in the practice of the instant invention, can be evidenced by activity in at least one of the protocols described hereinbelow. In general, the compounds exemplified in the Examples provided a range of activity from about 1 nM to about 10 μM using either the functional or binding assays described below.

Assay 1

$\beta_3$ Receptor Selectivity Over $\beta_1$ and $\beta_2$ Adrenergic Receptors In vitro $\beta_3$ receptor agonist activity and selectivity over $\beta_1$ and $\beta_2$ adrenergic receptors may be determined by measurement of cyclic adenosine monophosphate (cAMP) accumulation in Chinese hamster ovary cells (available from the American Type Culture Collection).

Chinese hamster ovary cells uniquely transfected with the cDNA for the human $\beta_1$, $\beta_2$, or $\beta_3$ adrenergic receptor are grown to confluence in Ham's F12 media (Gibco BRL, Life Technologies, Inc., Grand Island, N.Y.) containing 10% fetal bovine serum, 500 mg/mL geneticin, 100 U/mL penicillin, 100 mg/mL streptomycin, and 250 ng/mL fungizone according to the procedure described in American Type Culture Catalog of Cell Lines and Hybridomas, Seventh Edition, 1992, p. 36, ATCC CCL 61 CHO-K1. Compounds are prepared as 25 mM stock solutions in DMSO (0.1% DMSO final concentration), diluted in Ham's F12 media and added to the cells at $10^{-10}$ to $10^{-5}$ M along with $10^{-5}$ M isobutyl-methylxanthine to inhibit phosphodiesterase activity. The media and cells are then incubated for sixty minutes at 37° C. At the end of the incubation period, the media is aspirated and the cells lysed in 0.01 N HCl. The cellular content of cAMP is then determined by radioimmunoassay (RIA) using a kit from New England Nuclear (Burlington, Mass.). There is a direct correlation between the cellular content of cAMP and the agonism of the $\beta_1$, $\beta_2$, or $\beta_3$ adrenergic receptor. The non-selective, full β-adrenergic agonist isoproterenol is included as a positive control at $10^{-5}$ M. Each of the compounds listed in Examples 1–3 were tested in assay 1 and the compounds had a range of activity between 0.5 nM and 10 μm.

Assay 2

Many G protein-coupled receptors (GPCRs) exhibit at least two agonist affinity states. High affinity agonist binding to GPCRs requires the association or coupling of the receptor with the GDP-bound heterotrimeric G protein complex. In general, the low affinity agonist binding site is indicative of the uncoupled receptor state. The high affinity agonist binding site can be converted to the low affinity site by addition of GTP or its analogs. In the absence of agonist, G proteins display high affinity for GDP. In the presence of agonist, G proteins display high affinity for GTP. Thus, when agonist and GTP are added to the receptor/G protein complex, GTP displaces GDP and uncouples the receptor from the G protein. Two affinity states for agonists can be detected in radioligand competition binding assays. A two-site fit is generally observed for agonists for many GPCRs and can be calculated using commercially available software. The high affinity site ($K_{iH}$) corresponds to the G protein-coupled state and, in the case of $\beta_3$-adrenergic receptors correlates well with the functional $ED_{50}$ for stimulation of cAMP accumulation.

In order to identify compounds that attenuate the binding of [$^{125}$I]cyanopindolol (ICYP) to $\beta_3$ adrenergic receptors, the following radioligand binding assay can be used.

Radioligand Binding Assays
ICYP $\beta$3 Adrenergic Receptor Competition Binding Assay The specific activity of [$^{125}$I]ICYP is 2000 Ci/mmole. ICYP undergoes catastrophic decay upon radiolysis. Therefore, the specific activity always remains at 2000 Ci/mmole, but the concentration will decrease over time. The final concentration of ICYP is 250 pM. Therefore, a 2.5 nM (10×) stock needs to be made. [125I]CYP can be obtained from New England Nuclear, Boston, Mass.

Competitors

Up to four compounds can be tested in thirteen competition curves in a 96 well format. An example for a single compound is outlined below.

[Comp 1]
A 1,2 −10
B 1,2 −9.3
C 1,2 −9
D 1,2 −8.3
E 1,2 −8
F 1,2 −7.3
G 1,2 −7
H 1,2 −6.3
A 3,4 −6
B 3,4 −5
C 3,4 −4
D 1,3 pindolol
E 3,4 TOTAL The next compound would begin in F 3,4. Two pairs of totals and non-specific binding are added to the plates.
Wells E 3,4 and G 7,8 are for total cpm bound.
Wells D 3,4 and H 7,8 are for 100 $\mu$M pindolol to determine non-specific binding.

To Each Well in Order Add:
20 $\mu$l buffer to "total" wells
20 $\mu$l 1 mM pindolol to pindolol wells
20 $\mu$l of each concentration of compound to the appropriate wells
20 $\mu$l of 2.5 nM ICYP to all wells
160 $\mu$l membranes diluted to 15 $\mu$g/160 $\mu$l Procedure
1. Set up assay for Packard 96 well Unifilter with GF/C filters (Packard; Meriden, Conn.) using a 96 well microtiter plate.
2. Incubate 90–120 minutes with shaking at room temperature
3. Using Packard cell harvester (Packard; Meriden, Conn.), aspirate samples into processing head. Use a pre-soaked (0.3% PEI) filter.
4. Wash four times with cold wash buffer.
5. Dry plate, and add 25 II Microscint (ICN Manufacturers; Costa Mesa, Calif.) to each well.
6. Count samples in Wallac beta plate reader (Wallac; Turku, Finland).

Binding Buffer
50 mM Hepes/10 mM $MgCl_2$, pH 7.4 (prepared from 10×stock solution)
0.2% BSA (fraction V)
Protease inhibitors (prepared as 100×stock solution)
100 $\mu$g/mL bacitracin
100 $\mu$g/mL benzamidine
5 $\mu$g/mL aprotin
5 $\mu$g/mL leupeptin Wash Buffer
50 nM Hepes/10 mM $MgCl_2$, pH 7.4, ice cold (prepared from 10×stock solution)

Assay 3

Oxygen Consumption

As will be well known to one of ordinary skill in the art, during increased energy expenditure, animals generally consume increased amounts of oxygen. In addition, metabolic fuels such as, for example, glucose and fatty acids, are oxidized to $CO_2$ and $H_2O$ with the concomitant evolution of heat, an effect commonly referred to in the art as thermogenesis. Accordingly, the measurement of oxygen consumption in animals, including humans and companion animals, is an indirect measure of thermogenesis, and indirect calorimetry may be commonly used in animals, e.g., humans, by one of ordinary skill in the art, to measure such energy expenditures.

The ability of the compounds of the present invention to generate a thermogenic response may be demonstrated according to the following protocol using male Sprague-Dawley rats (Charles River, Wilmington, Mass.).

Whole animal oxygen consumption may be measured using an open circuit, indirect calorimeter (Oxymax™, Columbus Instruments, Columbus, Ohio.). The gas sensors are calibrated with nitrogen gas and gas mixture (0.5% carbon dioxide, 20.5% oxygen, 79% nitrogen; ABCO Industrial Supplies, Waterford, Conn.) before each experiment. Male Sprague-Dawley rats (300–380 g body weight) are placed in sealed chambers (43×43×10 cm) of the calorimeter and the chambers placed in activity monitors. Air flow rate through the chambers is set at 1.6–1.7 l/min. The calorimeter software calculates the oxygen consumption (mL/kg/hour) based on the flow rate of air through the chambers and the difference in oxygen content at inlet and outlet ports. The activity monitors have fifteen infrared light beams spaced one inch apart on each axis; ambulatory activity is recorded when two consecutive beams are broken (repeated interruptions of the same beam are not registered) and the results are recorded as counts. Basal oxygen consumption and ambulatory activity are measured every ten minutes for two and one-half to three hours. At the end of the basal period, the chambers are opened and the test compound (0.01–20 mg/kg, prepared in water, 0.5% methyl cellulose, or other suitable vehicle) or an equivalent amount of vehicle is administered by oral gavage. Oxygen consumption and amulatory activity are measured every ten minutes for an additional two to six hours post-dosing. Percent change in oxygen consumption is calculated by averaging the post-dosing values and dividing by basal oxygen consumption (average of the pre-dosing values except the first hour). Oxygen consumption values obtained during time periods where ambulatory activity exceeds 100 counts are excluded from the calculation. Thus, the values represent % change in resting oxygen consumption.

Assay 4
Hypoglycemic Activity

The compounds of the present invention may be tested for hypoglycemic activity according to the following procedure, and as an aid in determining dosages when compared to other test compounds and standards.

Five to eight-week old C57 BL/6J-ob/ob mice (Jackson Laboratory, Bar Harbor, Me.) are housed five animals per cage at an ambient temperature of 66 ° C. under standard animal care practices. After a one week acclimation period, the animals are weighed and 25 microliters of blood are collected via an ocular bleed prior to any treatment. The blood sample is immediately diluted 1:5 with saline containing 2% sodium heparin, in tubes held on ice. Blood samples are centrifuged for two minutes to remove red blood cells and the supernatant is analyzed for glucose concentration using a clinical autoanalyzer (Abbott Spectrum® CCx; Abbott Laboratories, Abbott Park, Ill.). Animals are then regrouped, in groups of five animals per cage, such that the mean glucose values of the groups are similar. The mice are then dosed once or twice daily for five days with test compound (0.01–20 mg/kg), with a positive control such as englitazone or ciglitazone (50 mg/kg p.o.) (U.S. Pat. No. 4,467,902; Sohda et al., Chem. Pharm. Bull., 32, 4460–4465, (1984)), or with vehicle. All compounds are administered by oral gavage in a vehicle consisting of 0.5% w/v methyl cellulose, or with other suitable vehicle. On Day 5, the animals are weighed again and bled (via the ocular route) for blood glucose levels as described hereinabove. Plasma glucose is then calculated by the equation:

Plasma Glucose (mg/dl)=Sample Value×5×1.67=8.35× Sample Value where 5 is the dilution factor and 1.67 is the plasma hematocrit adjustment (assuming the hematocrit is 40%).

The animals dosed with vehicle maintain substantially unchanged hyperglycemic glucose levels (e.g., 300 mg/dl), while positive control animals have depressed glucose levels (e.g., 130 mg/dl). The glucose lowering activities of test compounds are expressed in terms of % glucose normalization. For example, a glucose level which is the same as the positive control is expressed as 100%.

Assay 5
$\beta_1$ and $\beta_2$ Receptor Selectivity

In vivo selectivity for $\beta_1$ and $\beta_2$ receptors may be determined by measurements of heart rate, blood pressure, and plasma potassium concentration gathered on conscious catheterized rats (male, Sprague-Dawley, 300–400 g body weight). To implant catheters, rats are anesthetized with pentobarbital (50–60 mg/kg i.p.) and the left carotid artery is cannulated with PE50 tubing. The catheter is tunneled subcutaneously, exteriorized at the back of the neck, filled with a solution of polyvinylpyrrolidone in heparinzied saline, flame sealed, and taped. Experiments are performed seven days after surgery. On the day of the experiment, the catheters are untaped and flushed with saline. After at least thirty minutes, basal values for heart rate and blood pressure are measured by attaching the catheter to a pressure transducer, the results recorded on a Grass Model 7 polygraph (Grass Medical Instruments, Quincy, Mass.), and a basal blood sample (0.5 mL) is obtained from the arterial catheter. After obtaining basal values, the test compound or vehicle is administered by oral gavage and blood pressure (measure of $\beta_2$ activity) and heart rate (measure of $\beta_1$ activity) measurements are taken at 15, 30, 45, and 60 minutes, and blood samples for potassium determination ($\beta_2$) are obtained at 30 and 60 minutes. Isoproterenol, a non-selective $\beta$-agonist, can be tested as a positive control at doses ranging from 0.001 to 1 mg/kg (injected s.c. in saline vehicle). Plasma potassium is determined by flame spectrophotometry. To determine changes, basal values are subtracted from the average of the post-dosing values.

Assay 6
Reducing Intestinal Motility

The compounds of the present invention have the effect of reducing intestinal motility and thus have utility in aiding in the treatment of various gastrointestinal disorders such as irritable bowel syndrome, peptic ulceration, esophagitis, gastritis, duodenitis (including that induced by *Helicobacter pylon*), intestinal ulcerations (including inflammatory bowel disease, ulcerative colitis, Crohn's Disease and proctitis), and gastrointestinal ulcerations. It has been proposed that the motility of non-sphincteric smooth muscle contraction is mediated by activity at $\beta_3$ adrenergic receptors. The availability of a $\beta_3$ specific agonist, with little activity at $\beta_1$ and $\beta_2$ receptors, will assist in the pharmacologic control of intestinal motility without concurrent cardiovascular effects.

In vivo activity of the compounds of the present invention for the treatment or prevention of intestinal motility disorders can be determined according to the following procedures. Eighteen-hour fasted male Sprague-Dawley derived (CD) rats (175–225 g) are dosed with 0.01–20 mg/kg p.o. of test compound or vehicle (distilled water). Thirty minutes after administration of test compound, the rats are orally dosed with 0.25 mL of a solution of sodium chromate in 0.9% saline containing about 20,000 cpm of $^{51}Cr$ (specific activity 350 mCi/mg Cr). Twenty minutes later, the rats are sacrificed, the gastroesophageal, pyloric, and ileocecal junctions are then ligated, and the stomachs and small intestines are removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}Cr$ in each segment times the segments number: geometric center=S ((fraction of $^{51}Cr$ per segment)×(segment number)). For these calculations, the stomach is considered segment number 0, and the ten intestinal segments as numbers 1 to 10. Thus, a geometric center of 0.0 indicates that the entire load of $^{51}Cr$ remains in the stomach. Data from two experiments are pooled, and statistical evaluations are made using Dunnett's multiple comparison test.

Alternatively, in groups of eight, overnight-fasted male Sprague-Dawley (CD) rats (175–225 g) may be anesthetized with methoxyflurane. A small abdominal incision is then made, and the pylorus ligated. Immediately after the ligation, a solution of the test compound or vehicle (distilled water) is injected into the proximal duodenum. The doses of test compound used should be 0.01–20 mg/kg body weight. The incisions are then closed and the rats allowed to recover from the anesthesia. Two hours after the ligation, the rats are sacrificed and the gastric fluid collected and cleared by centrifugation. Total volume of secretion is determined by weight, and acidity is determined by titration to pH 7.0 with 0.1 N sodium hydroxide using an automatic titrator. The data from two experiments are then pooled. A group of rats treated with 10 mg/kg of of the anti-secretory histamine $H_2$-receptor antagonist cimetidine may be included as a positive control. Statistical evaluations can be made using Student's t-test.

In vitro activity for relaxation of contracted ileum from isolated guinea pig ileum is determined according to the following procedures. Fresh, isolated segments of guinea pig ileum (about 1.5 cm in length) are mounted in tissue baths containing Tyrode's physiological salt solution at about 30° C. and aerated continuously with oxygen:carbon dioxide (95%:5%). Tissues are then equilibrated for 60–90 minutes under 4.0 gm tension in order to achieve stable baselines. Histamine is then added to the baths and in a cumulative fashion in concentrations ranging from 1 nM to 10 mM. The maximum tension generated after each addition of histamine is recorded on a Grass Physiograph (Grass Medical Instruments, Quincy, Mass.). The tissues are then washed with several changes of Tyrode's solution, basal tension is readjusted to 4.0 gm, and a stable baseline is then again obtained. Each tissue is then exposed to a single concentration of a test compound (1 nM–10 mM) or vehicle and, after a thirty minute equilibration period, the histamine dose response curve is then repeated. Results from multiple experiments are standardized (0–100%) to the maximum response of the control tissues and plotted as percent maximum tension vs. the log of the histamine concentration in the absence and presence of the test compound.

Assay 7
Protection Against Gastric Ulceration

Food (but not water) is withheld from female Sprague-Dawley rats (Charles River, Wilmington, Mass.) weighing 70–120 g. Access is then permitted to food for ninety minutes. A single dose of test compound is then administered p.o. (0.01–20 mg/kg in a dosing volume of 1 mL/100 g), and indomethacin (Sigma Chemical Co., St. Louis, Mo.) (60 mg/kg, 1 mL/100 g body weight) is then injected subcutaneously. Control rats receive the subcutaneous injection of indomethacin and oral administration of vehicle (0.5% methyl cellulose in distilled water) for the test compound. The animals are then allowed continued access to food but water is withdrawn. The animals are then sacrificed by cervical dislocation six hours after dosing with indomethacin. The stomach are then removed, opened along the greater curvature and washed in 0.9% saline. An assessment of gastric damage is carried out by an observer who is unaware of the dosing regimen. A transparent plastic grid divided into 1 $mm^2$ sections is placed over the antrum and the area of macroscopic damage assessed as the total area of visible lesions in $mm^2$. This value is then expressed as a percentage of the total antral area.

Assay 8
Anti-Depressant Activity

Male CD1 mice weighing between 20 and 25 g and Sprague-Dawley rats weighing between 200 and 250 g are obtained from Charles River, Wilmington, Mass. Test compounds of the present invention are dissolved in water. The compounds are administered to mice in a volume of 10 mL/kg, and to rats in a volume of 2 mL/kg. Control animals receive the vehicle. Positive test results for the following parameters indicate anti-depressant activity.

(1) Antagonism of Hypothermia Induced by Reserpine

Mice are administered reserpine (2.5 mg/kg i.p. dissolved in 1% citric acid). Their rectal temperatures are measured three and one-half hours later. The mice are then divided into different groups so as to obtain the same mean rectal temperature in each group. One-half hour later, (i.e., four hours after reserpine administration), the mice are given the vehicle or test compound. Rectal temperature is measured again ninety minutes later (i.e., five hours and thirty minutes after reserpine administration) (Bourin, et al., The Value of the Reserpine Test in *Psychopharmacology, Arzneim. Forsch.*, 33, 1173, (1983)).

(2) Antagonism of Hypothermia Induced by Apomorphine

One-half hour after the mice are placed in individual cages, their rectal temperatures are recorded. The animals are allocated so as to obtain the same mean rectal temperature in each group. Apomorphine (16 mg/kg s.c.) is given thirty minutes after the test compound or vehicle. Rectal temperature is then measured again thirty minutes after the apomorphine treatment (Puech, et al., Antagonism of Hypothermia and Behavioral Response to Apomorphine; A Simple, Rapid, and Discriminating Test for Screening Anti-Depressants and Neuroleptics, *Psychopharmacology*, 75, 84, (1981)).

(3) Effect on Learned Helplessness Behavior

This test is performed essentially as described by Giral, et al., Reversal of Helpless Behavior in Rats by Putative 5-$HT_{1A}$ Agonists, Biol. Psychiat., 23, 237 (1988). Electric footshocks are delivered to male albino Sprague-Dawley rats placed in chambers (20×10×10) with Plexiglass® walls and covers. The floors are made of stainless-steel grids (1.5 cm mesh). A constant-current shock is delivered as sixty scrambled, randomized inescapable shocks (15 sec. duration, 0.8 mA, every 60+15 sec.) to the grid floor. Control rats are then placed in identical chambers, but no shock is administered. All preconditioning trials are performed on Day 1 between 9 and 11 a.m. Avoidance training is initiated 48 h (Day 3) after inescapable shock in automated two-way shuttle boxes (60×21×30 cm) with Plexiglass® walls and a floor consisting of stainless-steel rods spaced 1.0 cm apart in order to evaluate escape deficits. Each shuttle box is divided into two chambers of equal size by a stainless-steel partition with a gate providing access to the adjacent compartment through a 7×7 cm space. Shuttle box sessions are performed for three consecutive days (Days 3, 4, and 5). The animals are placed individually in the shuttle box and allowed to habituate to the environment for five minutes (for the first session only) and then subjected to thirty trials. The intertrial interval should be thirty seconds. A light signal, used as a conditioned stimulus, is presented during the first three seconds of each trial. Crossing the gate into the other compartment of the box during this "conditioned stimulus only" period (referred to as avoidance response) allows rats to avoid shocks. A period with conditioned stimulus plus foot-shock (0.8 mA) may be presented if an avoidance response does not occur. Crossing the gate into the other compartment during this conditioned stimulus plus shock period is referred to as an escape response. Absence of escape response during the three-second duration conditioned stimulus plus shock is considered to be an escape failure.

The rats (n=10 per group) are treated randomly according to one of the following protocols: the control sample, which receives no shock, and is given only vehicle, or experimental animals with inescapable shock are treated daily with vehicle or test compound. Animals are treated orally over five consecutive days, i.e. six hours after shock pretreatment on Day 1, and then twice per day, a half dose in the morning (30 minutes before shuttle box session) and half a dose in the afternoon (except on day 5). Statistical analysis is performed on the mean number of escape failures using a two-way analysis of variance (subjects×sessions) followed by Dunnett's test.

Assay 9
Bronchial Relaxation and Ciliary Motility

In vitro activity of the compounds of Formula (I) for the treatment of airway inflammatory disorders, such as asthma and obstructive lung disease, may be determined by measurement of guinea pig bronchial ring relaxation according to the following procedure.

Guniea pig bronchial rings are obtained from tri-colored guinea pigs of either sex (250–350 g), anesthized with urethane (1.25 g/kg) and suspended under an initial tension of 2.0 g in Krebs solution at 37° C. gassed with 95% oxygen:5% carbon dioxide. After about one hour of equilibration, the guinea pig bronchial rings are contracted with acetylcholine ($10^{-3}$ M), relaxed to maximal relaxation with theophylline ($10^{-3}$ M), and then allowed to equilibrate for a further sixty minutes while they are washed with Krebs solution every fifteen minutes.

Changes in tension are measured isometrically with strain guages and amplifiers and displayed on a recorder. The composition of the Krebs solution is (mM):NaCl 118.0, FCl 5.4, $CaCl_2$, 2.5, $KHPO_4$ 1.2, $MgSO_4$ 1.2, $NaHCO_3$ 25.0, and glucose 11.7.

To test effects of test compounds on resting tension, cumulative concentration-response curves are obtained by addition of the test compounds ($10^{-9}$–$10^{-6}$ M) every ten to twenty minutes until a plateau is reached. The relaxant effects of the test compounds are expressed as percentages of the maximal relaxations induced by theophylline (3×10M).

Assay 10
Prostate Disease

Ventral prostates of male Sprague-Dawley rats (300–400 g) anesthetized with diethyl ether are quickly excised and placed in oxygenated Krebs solution. While maintained at room temperature in this buffer, adherent fatty and connective tissues are removed. The prostates are then suspended in 10 mL organ baths containing Krebs solution warmed to 37° C. and aerated with a mixture of 95% oxygen and 5% carbon dioxide. The composition of the Krebs solution is 118.4 mM NaCl, 4.7 mM KCl, 1.2 mM $MgSO_4$, 2.5 mM $CaCl_2$, 11.1 mM dextrose, 25.0 mM $NaHCO_3$ and 1.2 mM $KH_2PO_4$, dissolved in distilled and demineralized water. The tissues are attached to isometric force-displacement transducers and isometric contraction is recorded under a loading tension of 0.5 g. Equilibration is undertaken for one or two hours before the addition of test compounds. Submaximal contractions are first elicited by repeated concentrations of $1\times10^{-6}$M phenylephrine until constant responses are obtained. The control and test compound-treated experiments are performed in different preparations. A concentration-response curve to cumulate concentrations of phenylephrine or acetylcholine ($10^{-9}$ to $10^{-4}$M) is determined. For testing compounds, a concentration response curve to phenylephrine or acetylcholine is determined in the presence of the compounds.

In vitro activity of compounds of Formula (I) can also be determined for specific efficacy in human prostate as follows.

Prostatic tissue specimens are obtained from patients with symptomatic BPH, who are undergoing open prostatectomy. Isolated human prostatic tissue is cut into five to eight strips (3 mm wide, 3 mm thick and 15 mm long in each strip). The strips are mounted vertically in organ baths containing 20 mL Krebs-Henseleit solution of the following composition (mM): NaCl 112, KCl 5.9, $MgCl_2$ 1.2, $CaCl_2$ 2, $NaHCO_3$ 25, $NaHPO_4$ 1.2, glucose 11.5. The medium is maintained at 37° C. and at pH 7.4, and is equilibrated with a gas mixture consisting of 95% oxygen and 5% carbon dioxide. A resting tension of 0.5g is applied and the responses are recorded isometrically through a force-displacement transducer. The preparations are equilibrated for ninety minutes before starting the experiments.

Concentration-response curves for phenylephrine or acetylcholine ($10^{-9}$ to $10^{-4}$M) are determined by adding the compound directly to the bathing media in a cumulative fashion. For testing compounds, the prostate strips are incubated in the presence of compound (1 or 1 $\mu$M) for thirty minutes before and then phenylephrine or acetylcholine are added to the medium in a cumulative fashion to obtain the concentration-response curve in the presence of the compound.

Assay 11
Effect on Trigylceride Levels and Dyslipidemia

Compounds of the present invention lower triglyceride levels and cholesterol levels and raise high density lipoprotein levels and are therefore of use in combating medical conditions wherein such lowering (and raising) is thought to be beneficial. Thus, the compounds of present invention can be used in the treatment of hypertriglyceridaemia, hypercholesterolemia, and conditions of low HDL (high density lipoprotein) levels in addition to the treatment of atherosclerotic disease such as of coronary, cerebrovascular and peripheral arteries, cardiovascular disease and related conditions.

Activity of compounds of the present invention for dyslipidemia can be determined according to the following procedure. C57BL/6J ob/ob mice (male, 30–40 g body weight, Jackson Lab, Bar Harbor, Me.), housed 5 mice per cage in an environmentally controlled room, are dosed once or twice daily for three weeks with test compound (0.01–20 mg/kg, n=15 per group) or vehicle (0.5% w/v methyl cellulose/distilled water, water, or other suitable vehicle) by oral gavage. At the end of the study, twenty-four hours after giving the final dose of compound, the mice are sacrificed by decapitation and blood collected. Plasma concentrations of free fatty acids and triglyceride are determined using a clinical autoanalyzer (Abbott Spectrum® CCx; Abbott Laboratories, Abbott Park, Ill.).

Assay 12
Decrease in Body Fat

Activity of compounds of the present invention for decrease in body fat can be determined according to the following procedure. C57BL/6J ob/ob mice (male, 30–40 g body weight, Jackson Lab, Bar Harbor, Me.) are housed five mice per cage in an environmentally controlled room with food (pelleted rodent chow) and water available ad libitum. The compound or vehicle (0.5% w/v methyl cellulose/distilled water, water, or other suitable vehicle) is dosed once or twice daily for three weeks (0.01–20 mg/kg, n=15 per group) by oral gavage. Body weight of each mouse is measured daily and food intake per cage determined by weighing the amount of food left in the trough. At the end of the study, twenty-four hours after giving the final dose of compound, the mice are weighed and then sacrificed by cervical dislocation. The epididymal fat pads from each mouse are excised and weighed. The fat versus body weight ratio is determined for each mouse using the absolute body weights and the fat pad weights. A reduction in fat pad weight is indicative of a reduction in total body fat.

What is claimed is:

1. A compound of Formula (I)

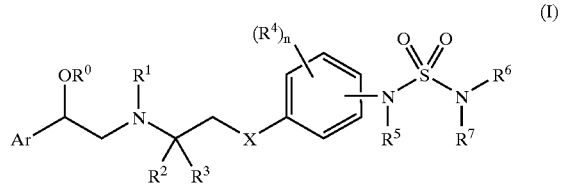

wherein

Ar is an unsubstituted or substituted aryl, or an unsubstituted or substituted heteroaryl;

$R^0$ is H, a hydroxy-protecting group, or taken together with $R^1$ forms a five membered ring;

$R^1$ is H, $(C_1–C_6)$alkyl, an amino-protecting group, or taken together with $R^0$ forms a five membered ring;

$R^2$, $R^3$ and $R^5$ are each independently H or $(C_1–C_6)$alkyl;

X is a covalent bond, O, $S(O)_p$, where p is 0, 1 or 2, or $NR^{1a}$, where $R^{1a}$ is H or $(C_1–C_6)$alkyl;

$R^4$ for each occurance is independently halo, unsubstituted or substituted $(C_1–C_6)$alkyl, cyano, or unsubstituted or substituted $(C_1–C_6)$alkoxy;

n is 0, 1, 2, or 3; and $R^6$ and $R^7$ are independently H, substituted or unsubstituted $(C_1–C_6)$alkyl, a substituted or unsubstituted, partially or fully saturated $(C_3–C_8)$cycloalkyl, a substituted or unsubstituted, partially or fully saturated $(C_3–C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a pharmaceutically acceptable salt thereof, or a solvate or hydrate of said compound or said salt.

2. The compound of claim 1 wherein $R^1$ and $R^5$ are hydrogen, and n is 0; a pharmaceutically acceptable salt thereof, or a solvate or hydrate of said compound or said salt.

3. The compound of claim 2 wherein Ar is pyridyl; a pharmaceutically acceptable salt thereof, or a solvate or hydrate of said compound or said salt.

4. The compound of claim 3 wherein said pyridyl is 3-pyridyl; a pharmaceutically acceptable salt thereof, or a solvate or hydrate of said compound or said salt.

5. The compound of claim 4 wherein $R^2$ and $R^3$ are hydrogen; a pharmaceutically acceptable salt thereof, or a solvate or hydrate of said compound or said salt.

6. The compound of claim 4 wherein $R^2$ and $R^3$ are methyl; a pharmaceutically acceptable salt thereof, or a solvate or hydrate of said compound or said salt.

7. The compound of claim 4 wherein X is a covalent bond; a pharmaceutically acceptable salt thereof, or a solvate or hydrate of said compound or said salt.

8. The compound of claim 4 wherein X is an oxygen; a pharmaceutically acceptable salt thereof, or a solvate or hydrate of said compound or said salt.

9. The compound of claim 5 wherein X is a covalent bond; a pharmaceutically acceptable salt thereof, or a solvate or hydrate of said compound or said salt.

10. The compound of claim 5 wherein X is an oxygen; a pharmaceutically acceptable salt thereof, or a solvate or hydrate of said compound or said salt.

11. The compound of claim 6 wherein X is a covalent bond; a pharmaceutically acceptable salt thereof, or a solvate or hydrate of said compound or said salt.

12. The compound of claim 2 wherein said Ar is a substituted phenyl, said substituted phenyl being a halogen substituted phenyl; a pharmaceutically acceptable salt thereof, or a solvate or hydrate of said compound or said salt.

13. The compound of claim 12 wherein said halogen substituted phenyl is 3-chlorophenyl a pharmaceutically acceptable salt thereof, or a solvate or hydrate of said compound or said salt.

14. The compound of claim 13 wherein X is a covalent bond; a pharmaceutically acceptable salt thereof, or a solvate or hydrate of said compound or said salt.

15. The compound of claim 13 wherein $R^2$ and $R^3$ are hydrogen a pharmaceutically acceptable salt thereof, or a solvate or hydrate of said compound or said salt.

16. The compound of claim 14 wherein $R^2$ and $R^3$ are hydrogen; a pharmaceutically acceptable salt thereof, or a solvate or hydrate of said compound or said salt.

17. A compound of Formula (IA)

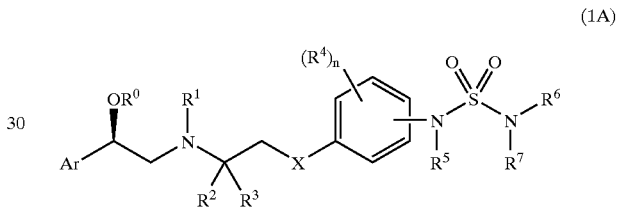

wherein

Ar is an unsubstituted or substituted aryl, or an unsubstituted or substituted heteroaryl;

$R^0$ is H, a hydroxy-protecting group, or taken together with $R^1$ forms a five membered ring;

$R^1$ is H, $(C_1–C_6)$alkyl, an amino-protecting group, or taken together with $R^0$ forms a five membered ring;

$R^2$, $R^3$ and $R^5$ are each independently H or $(C_1–C_6)$alkyl;

X is a covalent bond, O, $S(O)_p$, where p is 0, 1 or 2, or $NR^{1a}$, where $R^{1a}$ is H or $(C_1–C_6)$alkyl;

$R^4$ for each occurance is independently halo, unsubstituted or substituted $(C_1–C_6)$alkyl, cyano, or unsubstituted or substituted $(C_1–C_6)$alkoxy;

n is 0, 1, 2 or 3; and $R^6$ and $R^7$ are independently H, substituted or unsubstituted $(C_1–C_6)$alkyl, a substituted or unsubstituted, partially or fully saturated $(C_3–C_8)$cycloalkyl, a substituted or unsubstituted, partially or fully saturated $(C_3–C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a pharmaceutically acceptable salt thereof, or a solvate or hydrate of said compound or said salt.

18. The compound of claim 17 wherein $R^1$ and $R^5$ are hydrogen and n is 0; a pharmaceutically acceptable salt thereof, or a solvate or hydrate of said compound or said salt.

19. The compound of claim 18 wherein Ar is pyridyl; a pharmaceutically acceptable salt thereof, or a solvate or hydrate of said compound or said salt.

20. The compound of claim 19 wherein said pyridyl is 3-pyridyl; a pharmaceutically acceptable salt thereof, or a solvate or hydrate of said compound or said salt.

21. The compound of claim 20 wherein $R^2$ and $R^3$ are hydrogen; a pharmaceutically acceptable salt thereof, or a solvate or hydrate of said compound or said salt.

22. The compound of claim 20 wherein $R^2$ and $R^3$ are methyl; a pharmaceutically acceptable salt thereof, or a solvate or hydrate of said compound or said salt.

23. The compound of claim 20 wherein X is a covalent bond; a pharmaceutically acceptable salt thereof, or a solvate or hydrate of said compound or said salt.

24. The compound of claim 20 wherein X is an oxygen; a pharmaceutically acceptable salt thereof, or a solvate or hydrate of said compound or said salt.

25. The compound of claim 21 wherein X is a covalent bond; a pharmaceutically acceptable salt thereof, or a solvate or hydrate of said compound or said salt.

26. The compound of claim 21 wherein X is an oxygen; a pharmaceutically acceptable salt thereof, or a solvate or hydrate of said compound or said salt.

27. The compound of claim 22 wherein X is a covalent bond; a pharmaceutically acceptable salt thereof, or a solvate or hydrate of said compound or said salt.

28. The compound of claim 18 wherein said Ar is a substituted phenyl, said substituted phenyl being a halogen substituted phenyl; a pharmaceutically acceptable salt thereof, or a solvate or hydrate of said compound or said salt.

29. The compound of claim 28 wherein said halogen substituted phenyl is 3-chlorophenyl; a pharmaceutically acceptable salt thereof, or a solvate or hydrate of said compound or said salt.

30. The compound of claim 29 wherein X is a covalent bond; a pharmaceutically acceptable salt thereof, or a solvate or hydrate of said compound or said salt.

31. The compound of claim 29 wherein $R^2$ and $R^3$ are hydrogen; a pharmaceutically acceptable salt thereof, or a solvate or hydrate of said compound or said salt.

32. The compound of claim 30 wherein $R^2$ and $R^3$ are hydrogen; a pharmaceutically acceptable salt thereof, or a solvate or hydrate of said compound or said salt.

33. The compound of claim 30 wherein $R^2$ and $R^3$ are methyl; a pharmaceutically acceptable salt thereof, or a solvate or hydrate of said compound or said salt.

34. A compound selected from the group consisting of

N-[4-[2-[[(2R)-2-(3-chlorophenyl)-2-hydroxyethyl]amino]-2-methylpropyl]phenyl]-1-piperidinesulfonamide;

[4-[2-[[(2R)-2-(3-chlorophenyl)-2-hydroxyethyl]amino]ethyl]-phenyl]trimethyl-sulfamide;

N'-[4-[2-[[(2R)-2-(3-chlorophenyl)-2-hydroxyethyl]amino]ethyl]-phenyl]-N,N-dimethyl-sulfamide;

N-[4-[2-[[(2R)-2-(3-chlorophenyl)-2-hydroxyethyl]amino]ethyl]phenyl]-1-piperidinesulfonamide;

N-[4-[2-[[(2R)-2-(3-chlorophenyl)-2-hydroxyethyl]amino]ethyl]phenyl]-N'-cyclohexyl-sulfamide;

N'-[4-[2-[[(2R)-2-(3-chlorophenyl)-2-hydroxyethyl]amino]ethyl]phenyl]-N-cyclohexyl-N-sulfamide;

N-(cyclopropylmethyl)-N'-[4-[2-[[(2R)-2-hydroxy-2-(3-pyridinyl)ethyl]-amino]-2methylpropyl]phenyl]-sulfamide;

N-(1,1-dimethyl-2-phenylethyl)-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]-2-methylpropyl]-phenyl]-2,6-dimethyl-, (2R,6S)-4-morpholinesulfonamide;

N-[4-[2-[[(2R)-2-hydroxy-2-(3-pyridinyl)ethyl]amino]-2-methylpropyl]phenyl]-4-methyl-1-piperidinesulfonamide;

N-[4-[2-[[(2R)-2-hydroxy-2-(3-pyridinyl)ethyl]amino]-2-methylpropyl]-phenyl]-3,5-dimethyl-, (3R,5S)-1-piperidinesulfonamide;

N-[4-[2-[[(2R)-2-hydroxy-2-(3-pyridinyl)ethyl]amino]-2-methylpropyl]phenyl]-4-phenyl-1-piperidinesulfonamide;

N-[4-[2-[[(2R)-2-hydroxy-2-(3-pyridinyl)ethyl]amino]-2-methylpropyl]phenyl]-N'-[(1S)-1-phenylethyl]-sulfamide;

N-cyclohexyl-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]-2-methylpropyl]-phenyl]-octahydro-(4aR,8aR)-2(1H)-isoquinolinesulfonamide;

N-[4-[2-[[(2R)-2-hydroxy-2-(3-pyridinyl)ethyl]amino]-2-methylpropyl]phenyl]-N'-phenyl-sulfamide;

N'-[4-[2-[[(2R)-2-hydroxy-2-(3-pyridinyl)ethyl]amino]-2-methylpropyl]phenyl]-N,N-dimethyl-sulfamide;

N-(cyclohexylmethyl)-N'-[4-[2-[[(2R)-2-hydroxy-2-(3-pyridinyl)ethyl]amino]-2-methylpropyl]phenyl]-sulfamide;

N-cyclopropyl-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]-2-methylpropyl]-phenyl]-3-methyl-3-phenyl-1-piperidinesulfonamide;

N-[4-[2-[[(2R)-2-hydroxy-2-(3-pyridinyl)ethyl]amino]-2-methylpropyl]phenyl]-3,3-dimethyl-1-piperidinesulfonamide;

N-[4-[2-[[(2R)-2-hydroxy-2-(3-pyridinyl)ethyl]amino]-2-methylpropyl]-phenyl]-2,3-dihydro-spiro[1H-indene-1,3'-piperidine]-1'-sulfonamide;

N-[4-[2-[[(2R)-2-hydroxy-2-(3-pyridinyl)ethyl]amino]-2-methylpropyl]-phenyl]-N'-[(1R,2S)-2-phenylcyclopropyl]-sulfamide;

N-(2,3-dihydro-1H-inden-1-yl)-N'-[4-[2-[[(2R)-2-hydroxy-2-(3-pyridinyl)ethyl]amino]-2-methylpropyl]phenyl]-sulfamide;

N-(1R,2S,4S)-endo-bicyclo[2.2.1]hept-2-yl-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]-2-methylpropyl]phenyl]-N'-(2-methoxyethyl)-sulfamide;

N-[4-[2-[[(2R)-2-hydroxy-2-(3-pyridinyl)ethyl]amino]-2-methylpropyl]-phenyl]-N'-[[(2S)-tetrahydro-2-furanyl]methyl]-sulfamide;

N-[4-[2-[[(2R)-2-hydroxy-2-(3-pyridinyl)ethyl]amino]-2-methylpropyl]phenyl]-4-methyl-1-piperazinesulfonamide;

N-[4-[2-[[(2R)-2-hydroxy-2-(3-pyridinyl)ethyl]amino]-2-methylpropyl]-phenyl]-4-(phenylmethyl)-1-piperazinesulfonamide;

N-cyclobutyl-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]-2-methylpropyl]phenyl]-1-piperazinesulfonamide;

N-[4-[2-[[(2R)-2-hydroxy-2-(3-pyridinyl)ethyl]amino]-2-methylpropyl]-phenyl]-N'-[1-(phenylmethyl)-4-piperidinyl]-sulfamide;

N-[4-[2-[[(2R)-2-hydroxy-2-(3-pyridinyl)ethyl]amino]-2-methylpropyl]-phenyl]-N'-[(3S)-1-(phenylmethyl)-3-pyrrolidinyl]-sulfamide;

N-[4-[2-[[(2R)-2-hydroxy-2-(3-pyridinyl)ethyl]amino]-2-methylpropyl]-phenyl]-N'-[(1S,2S)-2-(phenylmethoxy)cyclopentyl]-sulfamide;

N'-[4-[2-[[(2R)-2-hydroxy-2-(3-pyridinyl)ethyl]amino]ethyl]phenyl]-N,N-dimethyl-sulfamide;

N-[4-[2-[[(2R)-2-hydroxy-2-(3-pyridinyl)ethyl]amino]ethyl]phenyl]-1-piperidinesulfonamide;

N-cyclohexyl-N'-[4-[2-[[(2R)-2-hydroxy-2-(3-pyridinyl)ethyl]amino]-ethyl]phenyl]-N-methyl-sulfamide;

N-[4-[2-[[(2R)-2-hydroxy-2-(3-pyridinyl)ethyl]amino]ethyl]phenyl]-4-(phenylmethyl)-1-piperidinesulfonamide;

N-[4-[2-[[(2R)-2-Hydroxy-2-(3-pyridinyl)ethyl]amino]ethyl]phenyl]-4-methyl-1-piperidinesulfonamide;

N-[4-[2-[[(2R)-2-hydroxy-2-(3-pyridinyl)ethyl]amino]ethyl]phenyl]-hexahydro-1H-azepine-1-sulfonamide;

N-[4-[2-[[(2R)-2-hydroxy-2-(3-pyridinyl)ethyl]amino]ethyl]phenyl]-2,6-dimethyl-, (2R,6S)-4-morpholinesulfonamide;

N'-[4-[2-[[(2R)-2-hydroxy-2-(3-pyridinyl)ethyl]amino]ethyl]phenyl]-N-methyl-N-(2-phenylethyl)-sulfamide;

N'-[4-[2-[[(2R)-2-hydroxy-2-(3-pyridinyl)ethyl]amino]ethyl]phenyl]-N-methyl-N-(1-methylethyl)-sulfamide;

N-[4-[2-[[(2R)-2-hydroxy-2-(3-pyridinyl)ethyl]amino]ethyl]phenyl]-3,4-dihydro-2(1H)-isoquinolinesulfonamide;

N-[4-[2-[[(2R)-2-hydroxy-2-(3-pyridinyl)ethyl]amino]ethyl]phenyl]-2-(methoxymethyl)-, (2S)-1-pyrrolidinesulfonamide;

N-[4-[2-[[(2R)-2-hydroxy-2-(3-pyridinyl)ethyl]amino]ethyl]phenyl]-3,5-dimethyl-, (3R,5S)-1piperidinesulfonamide;

N-(2,3-dihydro-1H-inden-2-yl)-N'-[4-[2-[[(2R)-2-hydroxy-2-(3-pyridinyl)ethyl]amino]ethyl]phenyl]-sulfamide;

N-[4-[2-[[(2R)-2-hydroxy-2-(3-pyridinyl)ethyl]amino]ethyl]phenyl]-4-phenyl-1-piperidinesulfonamide;

N'-[4-[2-[[(2R)-2-hydroxy-2-(3-pyridinyl)ethyl]amino]ethyl]phenyl]-N-methyl-N-phenyl-sulfamide;

4-(1,1-dimethylethyl)-N-[4-[2-[[(2R)-2-hydroxy-2-(3-pyridinyl)ethyl]amino]ethyl]phenyl]-1-piperidinesulfonamide;

N-[4-[2-[[(2R)-2-hydroxy-2-(3-pyridinyl)ethyl]amino]ethyl]phenyl]-octahydro-(4aS,8aS)-2(1H)-isoquinolinesulfonamide;

N-cyclohexyl-N'-[4-[2-[[(2R)-2-hydroxy-2-(3-pyridinyl)ethyl]amino]ethyl]phenyl]-sulfamide;

3-cyclohexyl-N-[4-[2-[[(2R)-2-hydroxy-2-(3-pyridinyl)ethyl]amino]ethyl]phenyl]-1-piperidinesulfonamide;

4-cyano-N-[4-[2-[[(2R)-2-hydroxy-2-(3-pyridinyl)ethyl]-amino]ethyl]phenyl]4-phenyl-1-piperidinesulfonamide;

N-[4-[2-[[(2R)-2-hydroxy-2-(3-pyridinyl)ethyl]amino]ethyl]phenyl]-3-[(4-methoxyphenyl)methyl]-1-pyrrolidinesulfonamide;

N-[(1R,2S,4S)-endo-bicyclo[2.2.1]hept-2-ylmethyl]-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]ethyl]phenyl]-5-methoxy-3,4-dihydro-spiro[naphthalene-1(2H),4'-piperidine]-1'-sulfonamide;

N-[4-[2-[[(2R)-2-hydroxy-2-(3-pyridinyl)ethyl]amino]ethyl]phenyl]-1-(4-methylphenyl)-3-azabicyclo[3.1.0]hexane-3-sulfonamide;

N-[4-[2-[[(2R)-2-hydroxy-2-(3-pyridinyl)ethyl]amino]ethyl]phenyl]-7-(trifluoromethyl)-1,2,4,5-tetrahydro-1,5-methano-3H-3-benzazepine-3-sulfonamide;

N'-[4-[2-[[(2R)-2-hydroxy-2-(3-pyridinyl)ethyl]amino]ethoxy]phenyl]-N,N-dimethyl-sulfamide; and N-[4-[2-[[(2R)-2-hydroxy-2-(3-pyridinyl)ethyl]amino]ethoxy]phenyl]-4-methyl-1-piperidinesulfonamide;

a pharmaceutically acceptable salt thereof, or a solvate or hydrate of said compound or said salt.

35. A compound selected from the group consisting of

N-[4-[2-[[(2R)-2-hydroxy-2-(3-pyridinyl)ethyl]amino]-2-methylpropyl]phenyl]-2R,6S-dimethyl-4-morpholinesulfonamide;

N-[4-[2-[[(2R)-2-hydroxy-2-(3-pyridinyl)ethyl]amino]ethyl]phenyl]-2(S)-(methoxymethyl)-1-pyrrolidinesulfonamide;

N-[4-[2-[[(2R)-2-hydroxy-2-(3-pyridinyl)ethyl]amino]ethyl]phenyl]-3,5-dimethyl-, (3R,5S)-1-piperidinesulfonamide;

N-[4-[2-[[(2R)-2-hydroxy-2-(3-pyridinyl)ethyl]amino]-2-methylpropyl]phenyl]-3,5-dimethyl-, (3R,5S)-1-piperidinesulfonamide;

N-cyclohexyl-N'-[4-[2-[[(2R)-2-hydroxy-2-(3-pyridinyl)ethyl]amino]-2-methylpropyl]phenyl]-sulfamide;

N-cyclopropyl-N'-[4-[2-[[(2R)-2-hydroxy-2-(3-pyridinyl)ethyl]amino]-2-methylpropyl]phenyl]-sulfamide;

N-[4-[2-[[(2R)-2-hydroxy-2-(3-pyridinyl)ethyl]amino]-2-methylpropyl]phenyl]-3-methyl-3-phenyl-1-piperidinesulfonamide;

N-[4-[2-[[(2R)-2-hydroxy-2-(3-pyridinyl)ethyl]amino]-2-methylpropyl]phenyl]-3,3-dimethyl-1-piperidinesulfonamide;

N-(cyclopropylmethyl)-N'-[4-[2-[[(2R)-2-hydroxy-2-(3-pyridinyl)ethyl]amino]-2-methylpropyl]phenyl]-sulfamide; and N-(1R,2S,4S)-endo-bicyclo[2.2.1]hept-2-yl-N'-[4-[2-[[(2R)-2-hydroxy-2-(3-pyridinyl)ethyl]amino]-2-methylpropyl]phenyl]-sulfamide;

a pharmaceutically acceptable salt thereof, or a solvate or hydrate of said compound or said salt.

36. A compound of Formula (I)

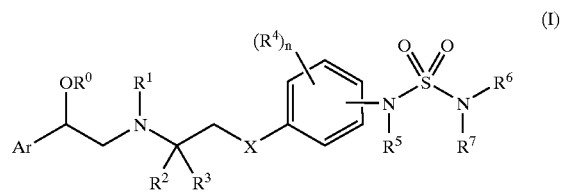

wherein

Ar is an unsubstituted or substituted aryl, or an unsubstituted or substituted heteroaryl;

$R^0$ and $R^1$ are hydrogen;

$R^2$, $R^3$ and $R^5$ are each independently H or $(C_1–C_6)$alkyl;

X is a covalent bond, O, $S(O)_p$, where p is 0, 1 or 2, or $NR^{1a}$, where $R^{1a}$ is H or $(C_1–C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2, or 3; and $R^6$ and $R^7$ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

prepared by deprotecting a compound of Formula (II)

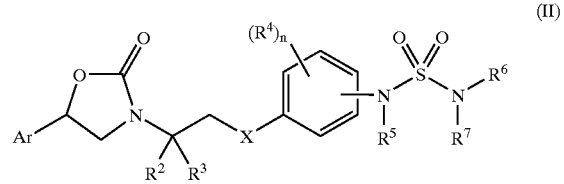

wherein $R^2$, $R^3$, $R^4$, $R^5$, $R^6$, $R^7$, Ar, X, and n are as defined above.

37. A compound of Formula (I)

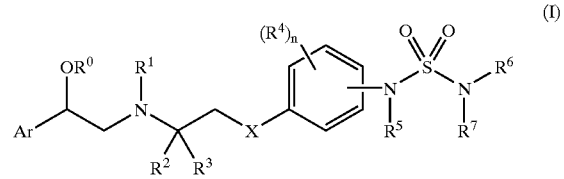

wherein

Ar is an unsubstituted or substituted aryl, or an unsubstituted or substituted heteroaryl;

$R^0$ and $R^1$ are hydrogen;

$R^2$, $R^3$ and $R^5$ are each independently H or $(C_1-C_6)$alkyl;

X is a covalent bond, O, $S(O)_p$, where p is 0, 1 or 2, or $NR^{1a}$, where $R^{1a}$ is H or $(C_1-C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2, or 3; and $R^6$ and $R^7$ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

prepared by deprotecting a compound of Formula (III)

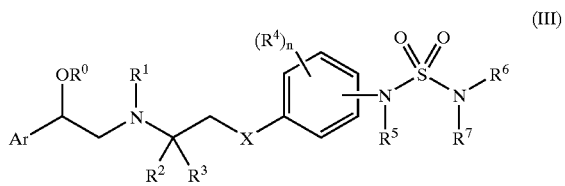

wherein $R^0$ is a hydroxy-protecting group; $R^1$ is H or an amino-protecting group; and $R^2$, $R^3$, $R^4$, $R^5$, $R^6$, $R^7$, Ar, X, and n are as defined above.

38. A method of treating a $\beta_3$ adrenergic receptor-mediated disease, condition, or disorder in an animal in need of such treatment comprising the step of administering to said animal a therapeutically effective amount of a compound of Formula (I)

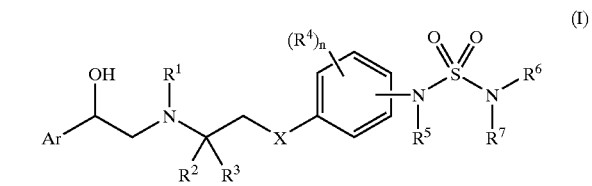

wherein

Ar is an unsubstituted or substituted aryl, or an unsubstituted or substituted heteroaryl;

$R^1$, $R^2$, $R^3$ and $R^5$ are each independently H or $(C_1-C_6)$alkyl;

X is a covalent bond, O, $S(O)_p$, where p is 0, 1 or 2, or $NR^{1a}$, where $R^{1a}$ is H or $(C_1-C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2, or 3; and $R^6$ and $R^7$ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a pharmaceutically acceptable salt thereof, or a solvate or hydrate of said compound or said salt, wherein said $\beta_3$ adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ulcer, gastritis, hypercholesterolemia, cardiovascular disease, urinary incontinence, depression, prostate disease, dyslipidemia, and airway inflammatory disorder.

39. The method of claim 38 wherein said compound of Formula (I) is a compound of Formula (IA)

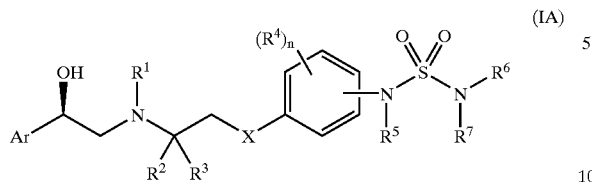

(IA)

wherein

Ar is an unsubstituted or substituted aryl, or an unsubstituted or substituted heteroaryl;

$R^1$ is hydrogen;

$R^2$, $R^3$ and $R^5$ are each independently H or $(C_1-C_6)$alkyl;

X is a covalent bond, O, $S(O)_p$, where p is 0, 1 or 2, or $NR^{1a}$, where $R^{1a}$ is H or $(C_1-C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2, or 3; and $R^6$ and $R^7$ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a pharmaceutically acceptable salt thereof, or a solvate or hydrate of said compound or said salt, wherein said $\beta_3$ adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ulcer, gastritis, hypercholesterolemia, cardiovascular disease, urinary incontinence, depression, prostate disease, dyslipidemia, and airway inflammatory disorder.

40. A method of increasing lean meat content in an edible animal comprising the step of administering to said edible animal a lean meat increasing amount of a compound of Formula (I)

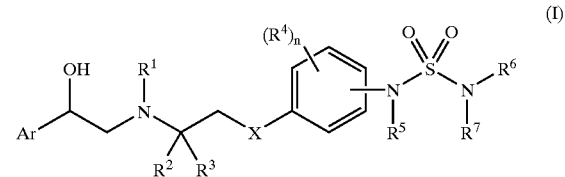

(I)

wherein

Ar is an unsubstituted or substituted aryl, or an unsubstituted or substituted heteroaryl;

$R^1$, $R^2$, $R^3$ and $R^5$ are each independently H or $(C_1-C_6)$ alkyl;

X is a covalent bond, O, $S(O)_p$, where p is 0, 1 or 2, or $NR^{1a}$, where $R^{1a}$ is H or $(C_1-C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2, or 3; and $R^6$ and $R^7$ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a pharmaceutically acceptable salt thereof, or a solvate or hydrate of said compound or said salt.

41. The method of claim 40 wherein said compound of Formula (I) is a compound of Formula (IA)

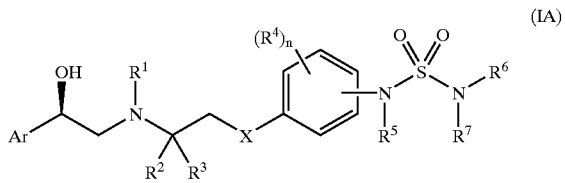

(IA)

wherein

Ar is an unsubstituted or substituted aryl, or an unsubstituted or substituted heteroaryl;

$R^1$ is hydrogen;

$R^2$, $R^3$ and $R^5$ are each independently H or $(C_1-C_6)$alkyl;

X is a covalent bond, O, $S(O)_p$, where p is 0, 1 or 2, or $NR^{1a}$, where $R^{1a}$ is H or $(C_1-C_6)$alkyl;

$R^4$ for each occurance is independently halo, unsubstituted or substituted $(C_1-C_6)$alkyl, cyano, or unsubstituted or substituted $(C_1-C_6)$alkoxy;

n is 0, 1, 2, or 3; and $R^6$ and $R^7$ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or $R^6$ and $R^7$ taken together form a substituted or unsubstituted, partially or fully saturated, heterocyclic 3 to 8 membered ring;

a pharmaceutically acceptable salt thereof, or a solvate or hydrate of said compound or said salt.

42. A pharmaceutical composition comprising (a) a pharmaceutically acceptable carrier, vehicle, diluent or mixture thereof; and (b) a compound of Formula (I)

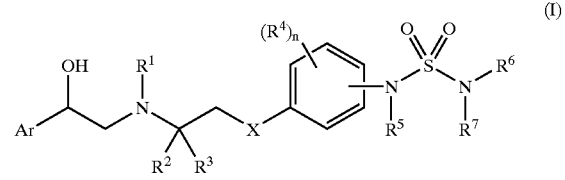

(I)

wherein

Ar is an unsubstituted or substituted aryl, or an unsubstituted or substituted heteroaryl;

$R^1$, $R^2$, $R^3$ and $R^5$ are each independently H or $(C_1-C_6)$ alkyl;

X is a covalent bond, O, $S(O)_p$, where p is 0, 1 or 2, or $NR^{1a}$, where $R^{1a}$ is H or $(C_1-C_6)$alkyl;

R⁴ for each occurance is independently halo, unsubstituted or substituted $(C_1-C_6)$alkyl, cyano, or unsubstituted or substituted $(C_1-C_6)$alkoxy;

n is 0, 1, 2, or 3; and

R⁶ and R⁷ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or R⁶ and R⁷ taken together form a substituted or unsubstituted, partially or fully saturated, heterocyclic 3 to 8 membered ring;

a pharmaceutically acceptable salt thereof, or a solvate or hydrate of said compound or said salt.

43. The composition of claim 42 wherein said compound of Formula (I) is a compound of Formula (IA)

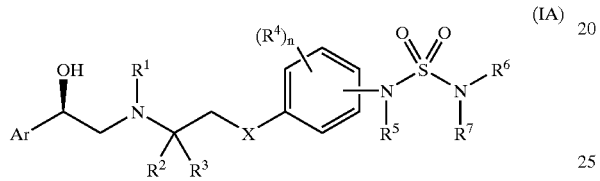

(IA)

wherein

Ar is an unsubstituted or substituted aryl, or an unsubstituted or substituted heteroaryl;

R¹, R², R³ and R⁵ are each independently H or $(C_1-C_6)$ alkyl;

X is a covalent bond, O, $S(O)_p$, where p is 0, 1 or 2, or $NR^{1a}$, where $R^{1a}$ is H or $(C_1-C_6)$alkyl;

R⁴ for each occurance is independently halo, unsubstituted or substituted $(C_1-C_6)$alkyl, cyano, or unsubstituted or substituted $(C_1-C_6)$alkoxy;

n is 0, 1, 2, or 3; and

R⁶ and R⁷ are independently H, substituted or unsubstituted $(C_1-C_6)$alkyl, a substituted or unsubstituted, partially or fully saturated $(C_3-C_8)$cycloalkyl, a substituted or unsubstituted, partially or fully saturated $(C_3-C_8)$ heterocyclic ring, a substituted or unsubstituted aryl, a substituted or unsubstituted heteroaryl, or R⁶ and R⁷ taken together form a substituted or unsubstituted, partially or fully saturated, heterocyclic 3 to 8 membered ring;

a pharmaceutically acceptable salt thereof, or a solvate or hydrate of said compound or said salt.

44. A method of treating a β₃ adrenergic receptor-mediated disease, condition, or disorder in an animal in need of such treatment comprising the step of administering to said animal a therapeutically effective amount of a composition of claim 42, wherein said β₃ adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ulcer, gastritis, hypercholesterolemia, cardiovascular disease, urinary incontinence, depression, prostate disease, dyslipidemia, and airway inflammatory disorder.

45. A method of treating a β₃ adrenergic receptor-mediated disease, condition, or disorder in an animal in need of such treatment comprising the step of administering to said animal a therapeutically effective amount of a composition of claim 43, wherein said β₃ adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ulcer, gastritis, hypercholesterolemia, cardiovascular disease, urinary incontinence, depression, prostate disease, dyslipidemia, and airway inflammatory disorder.

46. A method of increasing lean meat content in an edible animal comprising the step of administering to said edible animal a lean meat increasing amount of a pharmaceutical composition of claim 42.

47. A method of increasing lean meat content in an edible animal comprising the step of administering to said edible animal a lean meat increasing amount of a pharmaceutical composition of claim 43.

* * * * *